US007064323B2

(12) United States Patent
Yamakoshi et al.

(10) Patent No.: US 7,064,323 B2
(45) Date of Patent: Jun. 20, 2006

(54) CHEMICAL SUBSTANCE DETECTION APPARATUS AND CHEMICAL SUBSTANCE DETECTION METHOD

(75) Inventors: Hideo Yamakoshi, Kanagawa (JP); Hiroshi Futami, Kanagawa (JP); Minoru Danno, Kanagawa (JP); Shigenori Tsuruga, Kanagawa (JP); Shizuma Kuribayashi, Kanagawa (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 23 days.

(21) Appl. No.: 10/495,044

(22) PCT Filed: Jun. 27, 2003

(86) PCT No.: PCT/JP03/08237

§ 371 (c)(1), (2), (4) Date: May 11, 2004

(87) PCT Pub. No.: WO2005/001465

PCT Pub. Date: Jan. 6, 2005

(65) Prior Publication Data

US 2005/0009172 A1 Jan. 13, 2005

(51) Int. Cl.

| | |
|---|---|
| ***H01J 49/00*** | (2006.01) |
| ***B01D 59/44*** | (2006.01) |
| ***C12M 1/34*** | (2006.01) |

(52) U.S. Cl. ...................... 250/293; 250/281; 250/282; 250/283; 250/290; 250/291; 250/292; 435/287.2

(58) Field of Classification Search ........ 250/281–283, 250/290–292; 435/287.2
See application file for complete search history.

(56) References Cited

U.S. PATENT DOCUMENTS

| | | | | |
|---|---|---|---|---|
| 4,818,869 | A | 4/1989 | Weber-Grabau | |
| 5,324,939 | A * | 6/1994 | Louris et al. | 250/292 |
| 5,396,064 | A * | 3/1995 | Wells | 250/282 |
| 5,517,025 | A * | 5/1996 | Wells et al. | 250/282 |

(Continued)

FOREIGN PATENT DOCUMENTS

EP 1 291 651 A1 3/2003

(Continued)

OTHER PUBLICATIONS

S. Kuribayashi et al., “Real-Time Detection System for Trace-Level Chlorinated Organic Compounds”, Mitsubishi Heavy Industries Technical Review, vol. 38, No. 5, Sep. 30, 2001, pp. 262-265 and 286 (English translation, pp. 1-10).

(Continued)

*Primary Examiner*—John R. Lee
*Assistant Examiner*—Bernard E. Souw
(74) *Attorney, Agent, or Firm*—Foley & Lardner LLP

(57) ABSTRACT

A vacuum ultraviolet lamp ionizes a chemical substance contained in exhaust gas Gs. The chemical substance ionized is trapped in an ion trapping apparatus in which a radio frequency electric field is formed. Energy is applied to an ion group in the ion trapping apparatus with a SWIFT waveform comprising a frequency component excluding a frequency corresponding to an orbital resonance frequency of ions of the chemical substance to remove an impurity. Energy is then applied to the ion group with a TICKLE waveform having a frequency component corresponding to the orbital resonance frequency of the ions of the chemical substance to fragmentate the ions of the chemical substance. A mass of the fragment is then measured with a mass spectrometer to identify the chemical substance.

22 Claims, 10 Drawing Sheets

U.S. PATENT DOCUMENTS

| | | | | | |
|---|---|---|---|---|---|
| 5,521,380 | A * | 5/1996 | Wells et al. | 250/282 |
| 5,528,031 | A * | 6/1996 | Franzen | 250/282 |
| 5,808,299 | A * | 9/1998 | Syage | 250/288 |
| 5,843,311 | A | 12/1998 | Richter et al. | |
| 5,864,136 | A * | 1/1999 | Kelley et al. | 250/282 |
| 6,649,911 | B1 * | 11/2003 | Kawato | 250/293 |
| 6,828,549 | B1 * | 12/2004 | Schweikhard et al. | 250/281 |
| 6,847,037 | B1 * | 1/2005 | Umemura | 250/292 |
| 2003/0155505 | A1 * | 8/2003 | Russ et al. | 250/288 |
| 2005/0009172 | A1 * | 1/2005 | Yamakoshi et al. | 435/287.2 |
| 2005/0235678 | A1 * | 10/2005 | Lee et al. | 62/412 |

FOREIGN PATENT DOCUMENTS

| | | | |
|---|---|---|---|
| JP | 1-97350 | A | 4/1989 |
| JP | 7-14540 | A | 1/1995 |
| JP | 3032298 | B2 | 2/2000 |
| JP | 2001-235406 | A | 8/2001 |
| JP | 2002-181791 | A | 6/2002 |
| JP | 2003-203601 | A | 7/2003 |
| WO | WO 01/096852 | A1 | 12/2001 |

OTHER PUBLICATIONS

X. Jin et al., "On-Line Capillary Electrophoresis/Microelectrospray Ionization-Tandem Mass Spectrometry Using an Ion Trap Storage Time-of-Flight Mass Spectrometer with SWIFT Technology", Analytical Chemistry, vol. 71, No. 16, Aug. 15, 1999, pp. 3591-3597.

U. Schühle et al., "Sensitive Mass Spectrometry of Molecular Adsorbates by Stimulated Desorption and Single-Photon Ionization", J. Am. Chem. Soc., vol. 110, 1988, pp. 2323-2324.

L. He et al., "Development of Capillary High-performance Liquid Chromatography Tandem Mass Spectrometry System Using SWIFT Technology in an Ion Trap/Reflectron Time-of-flight Mass Spectrometer", Rapid Communications in Mass Spectrometry, vol. 11, 1997, pp. 1739-1748.

Y. Hori et al., "Analysis of Chlorophenol Monitored by an On-line Monitoring System for Dioxin Precursor in Flue Gas", Analysis II-Poster, Organohalogen Compounds, vol. 50, 2001, pp. 217-220.

M. Yamada et al., "An Online System for Monitoring Dioxin Precursor in Flue Gas", Analysis-Poster, Organohalogen Compounds, vol. 45, 2000, pp. 149-151.

* cited by examiner

CHEMICAL SUBSTANCE DETECTION APPARATUS AND CHEMICAL SUBSTANCE DETECTION METHOD

TECHNICAL FIELD

The present invention relates to a chemical substance detection apparatus and a method for measuring a chemical substance concentration, and more particularly to a chemical substance detection apparatus and a chemical substance detection method, which are used for detecting, with high accuracy, a dioxin or a precursor thereof contained in a very slight amount in the exhaust gas from, for example, a refuse incineration system.

BACKGROUND ART

Recently, for reducing dioxins contained in the exhaust gas from a refuse incineration system, attempts are being made to measure in real time dioxins or precursors thereof contained in the exhaust gas and use the measurement values for controlling combustion of the incineration furnace. The dioxins may be measured with high-resolution GC/MS (gas chromatography/mass spectrometer). However, this method requires cumbersome pretreatment and, currently, a time of from sampling to obtaining a result needs several weeks so that it is not practical to use this method where real-timeness is required. An on-line monitor is known in which dioxins or precursors thereof contained in exhaust gas are ionized by an atmospheric pressure chemical ionization method and the resultant ions are measured by means of a three-dimensional tetrode mass spectrometer. The on-line monitor has been described in detail in Abstracts of the 11th Conference 2000 of Japan Society of Waste Management Experts, and see the literature if necessary.

However, the atmospheric pressure chemical ionization method has the following problems. First, the sensitivity for measurement of molecules which are hardly changed to negative ions is low due to its measurement principle, and therefore the method is difficult to apply to control with high precision. The ionization probability of a chemical substance to be measured is largely affected by the gas composition of an atmosphere. Thus, for determining a concentration of the chemical substance from the measured electric signal intensity by making calculation, it is necessary to use a chemical substance containing an expensive C isotope as an internal standard sample, increasing the cost for the measurement.

In the atmospheric pressure chemical ionization method, generally, a phenol is detected wherein there is a correlation between a phenol and a dioxin with respect to the concentration and a phenol has relatively high sensitivity of measurement. However, the phenol is likely to be deposited on a pipe and therefore the memory effect is remarkable, and, for achieving a measurement with high sensitivity, piping is required to be improved with some contrivances. In addition, even in cleaned exhaust gas, a phenol is disadvantageously detected due to the memory effect, thereby lowering the accuracy of the measurement. Further, when a substance which is more easily ionized than the precursor to be measured is present in the exhaust gas, such a substance is first ionized, thus making it difficult to accurately measure the substance to be measured.

A certain precursor (e.g., trichlorophenol), which is an optimal index substance of the dioxin concentration for one furnace, is not always an optimal index substance for another furnace since there may be a difference between the one furnace and another with respect to the type of furnace or the conditions for combustion, and thus, the method which can measure a single precursor has only poor general-purpose properties. In other words, a method having improved general-purpose properties advantageously can detect various types of chemical substances simultaneously if possible.

DISCLOSURE OF THE INVENTION

It is an object of the present invention to solve at least the problems in the conventional technology.

A chemical substance detection apparatus according to an aspect of the present invention includes an ionization unit that applies to a chemical substance energy higher than an ionization potential of the chemical substance and lower than a sum of the ionization potential and dissociation energy of ions of the chemical substance to ionize the chemical substance; an ion trapping unit that traps, using any one of an electric field and a magnetic field, an ion group comprising the ions of the chemical substance formed by ionization by the ionization unit; an impurity removing unit that applies energy to the ion group by means of a SWIFT waveform comprising a frequency component excluding a frequency corresponding to an orbital resonance frequency of the ions of the chemical substance to remove an impurity from the chemical substance; and a mass analyzer that measures a mass of the chemical substance.

In the chemical substance detection apparatus according to the above-mentioned aspect, in ionization of a detection object chemical substance, energy higher than an ionization potential of the detection object chemical substance and lower than a sum of the ionization potential and dissociation energy of ions of the detection object chemical substance is applied to the detection object chemical substance. Therefore, the chemical substance to be detected can be ionized without being broken, making it possible to improve the ionization efficiency.

Further, a SWIFT waveform is merely applied for removing an impurity and hence, the impurity can be quickly removed. In the ionization according to the present invention, the energy required for ionization is appropriately adjusted, and hence various molecules do not unnecessarily suffer dissociation or ionization. Therefore, only a very few fragments are generated and the amount of impurities to be removed in the step of removing an impurity is extremely small, so that the SWIFT voltage can be lowered to allow the chemical substance to be detected to be left to remain unbroken, making it possible to improve the detection sensitivity of the mass analyzer. In addition, there is no need to prepare an excessively high power source and the production cost for the apparatus can be suppressed. Further, in the chemical substance detection apparatus according to the present invention, generation of excessive fragment ions can be considerably suppressed, thus making it possible to suppress a lowering of the trapping efficiency caused by an excess amount of ions present in the ion trap. As the mass analyzer, it is especially preferred to use one of a time-of-flight measurement mode since the time for measurement can be shortened. In the ion trapping unit, a unit that traps ions in the unit using an electric field, a magnetic field, or another electromagnetic force can be used. An electric field, a magnetic field, and other unit may be used individually or a plurality of these may be used in combination appropriately. As such an ion trapping unit, an ion trap in which a radio frequency electric field is formed is known, and this is preferred because the handling is relatively easy (this applies to the following).

The term "detection object chemical substance" here means a precursor of a dioxin or a dioxin contained in the exhaust gas from, for example, an incineration furnace. In the chemical substance detection apparatus according to the present invention, a dioxin concentration of the exhaust gas can be presumed by detecting a precursor having a good correlation with a dioxin. Alternatively, a dioxin contained in the exhaust gas can be directly detected to determine the dioxin concentration. The latter can be used for detecting a presumed value by a precursor. Dioxins generally include dioxins, furans, and molecules called coplanar PCB. The precursors include benzenes, such as trichlorobenzene, dichlorobenzene, and monochlorobenzene, and phenols, such as trichlorophenol.

In addition, SWIFT represents "Stored Waveform Inverse Fourier Transform". See "Development of a Capillary High-Performance Liquid Chromatography Tandem Mass Spectrometry System Using SWIFT Technology in an Ion Trap/Reflectron Time-of-flight Mass Spectrometer", Rapid Communication in mass spectrometry, vol. 11 1739–1748 (1997), for details.

A chemical substance detection apparatus according to another aspect of the present invention includes an ionization unit that applies to a chemical substance energy higher than an ionization potential of the chemical substance and lower than a sum of the ionization potential and dissociation energy of ions of the chemical substance to ionize the chemical substance; an ion trapping unit that traps, using any one of an electric field and a magnetic field, an ion group comprising the ions of the chemical substance formed by ionization by the ionization unit; an impurity removing unit that applies energy to the ion group by means of a SWIFT waveform comprising a frequency component excluding a frequency corresponding to an orbital resonance frequency of the ions of the chemical substance to remove an impurity from the chemical substance; a fragmentation unit that applies energy to the ion group by means of a TICKLE waveform comprising a frequency component corresponding to the orbital resonance frequency of the ions of the chemical substance to fragmentate the ions of the chemical substance; and a mass analyzer that measures a mass of a fragment of the chemical substance.

In the chemical substance detection apparatus according to the above-mentioned aspect, fragmentation of the detection object chemical substance is performed by means of a fragmentation unit that applies a TICKLE waveform. Therefore, even when an impurity is present in a frequency band corresponding to the mass number of the detection object chemical substance, the effect of the impurity can be removed to achieve an accurate measurement. In addition, only a very few fragments are generated in the ionization and therefore, in the fragmentation of the detection object chemical substance, the desired detection object chemical substance can be efficiently subjected to fragmentation. Accordingly, almost all the fragments of the detection object chemical substance can be subjected to measurement of the mass analyzer, and therefore the detection sensitivity of the mass analyzer can be improved and the combustion can be controlled with higher precision. The TICKLE is an operation for subjecting a detection object chemical substance to fragmentation and separating the detection object chemical substance from an impurity having a mass number close to that of the detection object chemical substance. See "Development of a Capillary High-Performance Liquid Chromatography Tandem Mass Spectrometry System Using SWIFT Technology in an Ion Trap/Reflectron Time-of-flight Mass Spectrometer", Rapid Communication in mass spectrometry, vol. 11 1739–1748 (1997), for details.

In the chemical substance detection apparatus, the ionization unit applies to the chemical substance energy higher than the ionization potential and equal to or smaller than a value of a sum of the ionization potential and 4 electron volts. Furthermore, the ionization unit is a light generation unit that generates light having a wavelength of 50 to 200 nanometers. Moreover, the ionization unit is a vacuum ultraviolet lamp.

It is preferable that the energy applied to the detection object chemical substance by the ionization unit is higher than the ionization potential and equal to or smaller than a value of a sum of the ionization potential and 4 electron volts. When the detection object chemical substance is ionized by energy of light, the wavelength of the light is 50 to 200 nanometers. Such a light is preferred since it can be easily obtained using a vacuum ultraviolet lamp.

A chemical substance detection apparatus according to still another aspect of the present invention includes an ion trapping unit that traps, using any one of an electric field and a magnetic field, an ion group comprising ions of a chemical substance formed by ionization; an arbitrary waveform generation unit that generates a SWIFT waveform having a voltage amplitude in a frequency corresponding to an orbital resonance frequency of an impurity present in a concentration such that it exhibits a signal intensity higher than a predetermined signal intensity, wherein the voltage amplitude is larger than a voltage amplitude in a frequency band corresponding to an orbital resonance frequency of the impurity present in a concentration such that it exhibits a signal intensity lower than a predetermined signal intensity; and a mass analyzer that applies the SWIFT waveform generated in the arbitrary waveform generation unit to the ion group trapped by the ion trapping unit to remove the impurity, and then measures a mass of the chemical substance or a fragment thereof.

In the chemical substance detection apparatus according to the above-mentioned aspect, an impurity in an especially high concentration can be selectively removed by using a SWIFT waveform in which the voltage amplitude in a frequency corresponding to the mass number of an impurity present in a concentration higher than a specific signal intensity is increased and the voltage amplitude in a frequency corresponding to the mass number of an impurity present in a lower concentration is lowered. Thus, an impurity can be selectively removed and therefore only small energy is required for SWIFT. In addition, a power source apparatus can be reduced in size, and there is no need to use an excessively high power source and this is advantageous from an economical point of view. It is preferred that the impurity for which the voltage amplitude of a SWIFT waveform is increased is an impurity present in such a concentration that it exhibits at least a signal intensity substantially equivalent to the signal intensity of the detection object chemical substance. The impurity may be an impurity present in a further smaller mass number, but larger energy is required for SWIFT in such a case, and therefore it is preferred that the impurity is an impurity having a signal intensity 50 percent or more of the signal intensity of the detection object chemical substance.

A chemical substance detection apparatus according to still another aspect of the present invention includes an ion trapping unit that traps, using any one of an electric field and a magnetic field, an ion group comprising ions of a chemical substance formed by ionization; an arbitrary waveform generation unit that generates a SWIFT waveform in which a voltage amplitude is reduced as a frequency is increased; and a mass analyzer that applies the SWIFT waveform to the ion group trapped by the ion trapping unit to remove the impurity, and then measures a mass of the chemical substance or a fragment thereof.

In the chemical substance detection apparatus according to the above-mentioned aspect, the energy applied to an impurity having a larger mass number is higher than the energy applied to an impurity having a smaller mass number. Generally, the orbital resonance frequency in an ion trap is a function of a mass number, and, the larger the mass number, the smaller the frequency, or the smaller the frequency interval corresponding to the mass number interval 1. On the other hand, in the formation of a SWIFT waveform generally conducted in, for example, the literature, "Development of a Capillary High-Performance Liquid Chromatography Tandem Mass Spectrometry System Using SWIFT Technology in an Ion Trap/Reflectron Time-of-flight Mass Spectrometer". Rapid Communication in mass spectrometry, vol. 11 1739–1748 (1997), a SWIFT waveform is formed by subjecting a frequency spectrum having a fixed voltage amplitude to inverse Fourier transform to convert it to a time region. In this case, a waveform synthesized from waveforms having a fixed voltage amplitude at fixed frequency intervals is formed. Therefore, in this case, the larger the mass number, the smaller the number of the sinusoidal wave per mass number interval 1, and hence energy per mass number interval 1 is small. In other words, the energy applied to a molecule having a larger mass number becomes relatively small.

By contrast, in the chemical substance detection apparatus according to the above-mentioned aspect, the voltage amplitude of the sinusoidal wave is increased for making up for the reduced number of the sinusoidal wave, and therefore satisfactory energy can be also applied to ions having large mass numbers, so that even such impurities can be surely removed. In addition, energy in a required and satisfactory range can be applied to ions having small mass numbers and therefore the use efficiency of the energy can be improved. Further, an excessively high power source apparatus is not required, and hence the cost for the apparatus can be suppressed.

A chemical substance detection apparatus according to still another aspect of the present invention includes an ion trapping unit that traps, using any one of an electric field and a magnetic field, an ion group comprising ions of a chemical substance formed by ionization; an arbitrary waveform generation unit that generates a SWIFT waveform in which a voltage amplitude has a fixed distribution, irrespective of a mass number of a molecule to be removed by SWIFT; and a mass analyzer that applies the SWIFT waveform to the ion group trapped by the ion trapping unit to remove an impurity, and then measures a mass of the chemical substance or a fragment thereof.

The chemical substance detection apparatus according to the above-mentioned aspect is such that, when the frequency spectrum of a SWIFT waveform in which the voltage amplitude is increased as the frequency is smaller is converted so that the mass number is taken as an abscissa, the voltage amplitude per unit mass number is a substantially fixed value. Thus, substantially the same energy can be applied to molecules having any masses to be removed by SWIFT. Therefore, satisfactory energy can be also applied to ions having large mass numbers, and hence even such impurities can be surely removed. Further, an excessively high power source apparatus is not required, and hence the cost for the apparatus can be suppressed.

A chemical substance detection apparatus according to still another aspect of the present invention includes an ion trapping unit that traps, using any one of an electric field and a magnetic field, an ion group comprising ions of a chemical substance formed by ionization; an arbitrary waveform generation unit that generates a SWIFT waveform which gives no voltage amplitude in a plurality of frequency bands corresponding to mass numbers of a plurality of chemical substances, and which gives a voltage amplitude in a frequency band corresponding to a mass number of an impurity; a fragmentation unit that applies energy to the ion group by means of a TICKLE waveform having a plurality of frequency components corresponding to orbital resonance frequencies of the chemical substances to fragmentate the ions of the chemical substances; and a mass analyzer that applies the SWIFT waveform to the ion group trapped by the ion trapping unit to remove the impurity, and then measuring masses of the chemical substances or fragments thereof.

The amount of a dioxin or a precursor thereof contained in the exhaust gas from an incineration furnace is very slight, and an improvement of the detection accuracy therefor is very important when the conditions for combustion of the incineration furnace are controlled in real time. In the chemical substance detection apparatus according to the present invention, an impurity is removed using a SWIFT waveform which gives no voltage amplitude in the frequency bands corresponding to a plurality of detection object chemical substances. In addition, the detection object chemical substances are detected simultaneously by the mass analyzer. Thus, a plurality of detection object chemical substances are detected simultaneously and; therefore, a measurement with high accuracy can be achieved and the precision of the combustion control can be improved.

The chemical substance detection apparatus further includes an ionization unit that applies to the chemical substance energy higher than an ionization potential of the chemical substance and lower than a sum of the ionization potential and dissociation energy of ions of the chemical substance to ionize the chemical substance. Moreover, the ionization unit applies to the chemical substance energy higher than the ionization potential and equal to or smaller than a value of a sum of the ionization potential and 4 electron volts.

In the chemical substance detection apparatus according to the above-mentioned aspect, energy higher than the ionization potential of the detection object chemical substance and lower than the dissociation energy is applied to the detection object chemical substance to ionize the detection object chemical substance. Therefore, unnecessary fragments are not generated, and the detection object chemical substance to be left is allowed to remain unbroken, making it possible to improve the detection sensitivity of the mass analyzer. By virtue of this effect as well as the above-mentioned action and effect obtained by the chemical substance detection apparatus, the detection sensitivity of the mass analyzer is further improved, enabling a measurement with high accuracy. In addition, the combustion of an incineration furnace can be controlled with higher precision. Further, the SWIFT voltage can be lowered, and therefore there is no need to prepare an excessively high power source and the production cost for the apparatus can be suppressed.

A chemical substance detection method according to still another aspect of the present invention includes an ionization step of applying to a chemical substance energy higher than an ionization potential of the chemical substance and lower than a sum of the ionization potential and dissociation energy of ions of the chemical substance to ionize the chemical substance; an ion trapping step of trapping, using any one of an electric field and a magnetic field, an ion group comprising the ions of the chemical substance formed by ionization at the ionization step; an impurity removing step of applying energy to the ion group by means of a SWIFT waveform comprising a frequency component excluding a frequency corresponding to an orbital resonance frequency of the ions of the chemical substance to remove an impurity from the chemical substance; and a mass analyzing step of measuring a mass of the chemical substance.

In the chemical substance detection method according to the above-mentioned aspect, when an impurity is to be removed, energy higher than the ionization potential of a detection object chemical substance and lower than the dissociation energy is applied to the detection object chemical substance. Therefore, an impurity can be removed while allowing the detection object chemical substance to remain unbroken, and generation of unnecessary fragment ions can be considerably suppressed during the removal of an impurity. Accordingly, the detection object chemical substance to be left can be allowed to remain unbroken, making it possible to improve the detection sensitivity of the mass analyzer. Further, a SWIFT waveform is merely applied for removing an impurity and hence, the impurity can be quickly removed. In addition, in the ionization according to the present invention, only a very few fragments are generated and the amount of impurities to be removed in the step of removing an impurity is extremely small, so that the SWIFT voltage can be lowered, and hence there is no need to prepare an excessively high power source, and the production cost for the apparatus can be suppressed.

A chemical substance detection method according to still another aspect of the present invention includes an ionization step of applying to a chemical substance energy higher than an ionization potential of the chemical substance and lower than a sum of the ionization potential and dissociation energy of ions of the chemical substance to ionize the chemical substance; an ion trapping step of trapping, using any one of an electric field and a magnetic field, an ion group comprising the ions of the chemical substance formed by ionization at the ionization step; an impurity removing step of applying energy to the ion group by means of a SWIFT waveform comprising a frequency component excluding a frequency corresponding to an orbital resonance frequency of the ions of the chemical substance to remove an impurity from the chemical substance; a fragmentation step of applying energy to the ion group by means of a TICKLE waveform comprising a frequency component corresponding to the orbital resonance frequency of the ions of the chemical substance to fragmentate the ions of the chemical substance; and a mass analyzing step of measuring a mass of a fragment of the chemical substance.

In the chemical substance detection method according to the above-mentioned aspect, fragmentation of the detection object chemical substance is conducted by applying a TICKLE waveform to the detection object chemical substance. Therefore, even when an impurity is present in a frequency band corresponding to the mass number of the detection object chemical substance, the effect of the impurity can be removed to achieve an accurate measurement. In addition, only very few fragments are generated in the ionization and therefore, in the fragmentation of a detection object chemical substance, the desired detection object chemical substance can be efficiently subjected to fragmentation. Accordingly, almost all the fragments of the detection object chemical substance can be subjected to mass analysis, so that the detection sensitivity of analysis in the mass analyzer can be improved. By this detection method, in controlling the conditions for combustion of an incineration furnace, the combustion can be controlled with higher precision.

A chemical substance detection method according to still another aspect of the present invention includes an ion trapping step of trapping, using any one of an electric field and a magnetic field, an ion group comprising ions of a chemical substance formed by ionization; an impurity removing step of measuring a distribution of an impurity contained in the ion group and applying to the ion group a SWIFT waveform comprising a frequency component corresponding to an impurity present in a predetermined ratio or more to remove the impurity; and a mass analyzing step of measuring a mass of the chemical substance or a fragment thereof.

In the chemical substance detection method according to the above-mentioned aspect, an impurity present in a predetermined ratio or more is selectively removed. Therefore, the energy needed for removing the impurity in a required and satisfactory amount is small, as compared to the energy needed for removing all the impurities. Therefore, a power source apparatus can be reduced in size and this is advantageous from an economical point of view. It is preferred that the impurity in a predetermined ratio is an impurity present with at least a signal intensity substantially equivalent to the signal intensity of the detection object chemical substance. The impurity may be an impurity having a further smaller signal intensity, but larger energy is required for SWIFT in such a case, and therefore it is preferred that the impurity is an impurity having a signal intensity 50 percent or more of the signal intensity of the detection object chemical substance.

A chemical substance detection method according to still another aspect of the present invention includes an ion trapping step of trapping, using any one of an electric field and a magnetic field, an ion group comprising ions of a chemical substance formed by ionization; an arbitrary waveform generation step of generating a SWIFT waveform having a voltage amplitude in a frequency corresponding to an orbital resonance frequency of an impurity present in a concentration such that it exhibits a signal intensity higher than a predetermined signal intensity, wherein the voltage amplitude is larger than a voltage amplitude in a frequency band corresponding to an orbital resonance frequency of the impurity present in a concentration such that it exhibits a signal intensity lower than a predetermined signal intensity; and a mass analyzing step of applying the SWIFT waveform generated in the arbitrary waveform generation unit to the ion group trapped in the ion trapping step to remove the impurity, and then measuring a mass of the chemical substance or a fragment thereof.

In the chemical substance detection apparatus according to the above-mentioned aspect, the voltage amplitude of a SWIFT waveform in a frequency corresponding to the mass number of an impurity present in a high concentration such that it exhibits a signal intensity higher than a specific signal intensity is increased, and the voltage amplitude for an impurity in a low concentration is lowered. Therefore, an impurity in an especially high concentration can be selectively removed. An impurity can be selectively removed and hence only small energy is required for SWIFT. Thus, only small energy is required for SWIFT, and a power source apparatus can be reduced in size and there is no need to use an excessively high power source, and this is advantageous from an economical point of view. It is preferred that the impurity for which the voltage amplitude of a SWIFT waveform is increased is an impurity having at least a signal intensity substantially equivalent to the signal intensity of the detection object chemical substance. The impurity may be an impurity present in a further smaller mass number, but larger energy is required for SWIFT in such a case, and therefore it is preferred that the impurity is an impurity having a signal intensity 50 percent or more of the signal intensity of the detection object chemical substance.

A chemical substance detection method according to still another aspect of the present invention includes an ion trapping step of trapping, using any one of an electric field and a magnetic field, an ion group comprising ions of a chemical substance formed by ionization; an impurity removing step of applying a SWIFT waveform in which a voltage amplitude is reduced as a frequency is increased to remove an impurity from the chemical substance; and a mass analyzing step of measuring a mass of the chemical substance or a fragment thereof.

In the chemical substance detection method according to the present invention, the energy applied to an impurity having a larger mass number is higher than the energy applied to an impurity having a smaller mass number. Generally, the orbital resonance frequency in an ion trap is a function of a mass number, and, the larger the mass number, the smaller the frequency, or the smaller the frequency interval corresponding to the mass number interval 1. On the other hand, in the formation of a SWIFT waveform generally conducted in, for example, the literature "Development of a Capillary High-Performance Liquid Chromatography Tandem Mass Spectrometry System Using SWIFT Technology in an Ion Trap/Reflectron Time-of-flight Mass Spectrometer", Rapid Communication in mass spectrometry, vol. 11 1739–1748 (1997), a SWIFT waveform is formed by subjecting a frequency spectrum having a fixed voltage amplitude to inverse Fourier transform to convert it to a time region. In this case, a waveform synthesized from waveforms having a fixed voltage amplitude at fixed frequency intervals is formed. Therefore, in this case, the larger the mass number, the smaller the number of the sinusoidal wave per mass number interval 1, and hence energy per mass number interval 1 is small. In other words, the energy applied to a molecule having a larger mass number becomes relatively small.

By contrast, in the present invention, the voltage amplitude of the sinusoidal wave is increased for making up for the relatively small energy, and therefore satisfactory energy can be also applied to ions having large mass numbers, so that even such impurities can be surely removed. Further, an excessively high power source apparatus is not required, and hence the cost for the apparatus can be suppressed.

A chemical substance detection method according to still another aspect of the present invention includes an ion trapping step of trapping, using any one of an electric field and a magnetic field, an ion group comprising ions of a chemical substance formed by ionization; an arbitrary waveform generation step of generating a SWIFT waveform in which a voltage amplitude has a fixed distribution, irrespective of a mass number of a molecule to be removed by SWIFT; and a mass analyzing step of applying the SWIFT waveform to the ion group trapped at the ion trapping step to remove an impurity, and then measures a mass of the chemical substance or a fragment thereof.

This chemical substance detection method is such that, when the frequency spectrum of a SWIFT waveform in which the voltage amplitude is increased as the frequency is smaller is converted so that the mass number is taken as an abscissa, the voltage amplitude per mass number is a substantially fixed value. Thus, substantially the same energy can be applied to molecules having any masses to be removed by SWIFT. Therefore, satisfactory energy can be also applied to ions having large mass numbers, and hence even such impurities can be surely removed. Further, an excessively high power source apparatus is not required, and hence the cost for the apparatus can be suppressed.

A chemical substance detection method according to still another aspect of the present invention includes an ion trapping step of trapping, using any one of an electric field and a magnetic field, an ion group comprising ions of a chemical substance formed by ionization; a step of applying to the ion group a SWIFT waveform which gives no voltage amplitude in a plurality of frequency bands corresponding to mass numbers of a plurality of chemical substances to remove an impurity while leaving the chemical substances; and a mass analyzing step of measuring masses of the chemical substances or fragments thereof.

The amount of a dioxin or a precursor thereof contained the exhaust gas from an incineration furnace is very slight, and an improvement of the detection accuracy therefor is very important when the conditions for combustion of the incineration furnace are controlled in real time. In the chemical substance detection method according to the present invention, an impurity is removed using a SWIFT waveform which gives no voltage amplitude in the frequency bands corresponding to a plurality of detection object chemical substances. In addition, the detection object chemical substances are detected simultaneously by the mass analyzer. Thus, a plurality of detection object chemical substances are detected simultaneously and therefore, for example, even when the accuracy of detection of the individual detection object chemical substances is unsatisfactory, a plurality of substances are collectively examined from the correlation with dioxins or evaluated with respect to the combustion state to achieve a measurement with higher accuracy, and the precision of the combustion control can be improved.

A chemical substance detection method according to still another aspect of the present invention includes an ion trapping step of trapping, using any one of an electric field and a magnetic field, an ion group comprising ions of a plurality of chemical substances having different masses formed by ionization; a step of applying to the ion group a SWIFT waveform which gives no voltage amplitude in a plurality of frequency bands corresponding to mass numbers of a plurality of chemical substances to remove an impurity while leaving the chemical substances; and a fragmentation step of fragmenting the chemical substance in an order of from a chemical substance having a smaller mass number to a chemical substance having a larger mass number; a mass analyzing step of measuring masses of the chemical substances or the fragments thereof.

In the chemical substance detection method according to the present invention, a plurality of detection object chemical substances are successively subjected to fragmentation in the order of from a detection object chemical substance having a smaller mass number to those having larger one. Therefore, the fragmentation of the detection object chemical substance having a small mass number makes it possible to prevent the fragment of a substance having a mass number larger than that of the detection object chemical substance from being broken. Thus, all the detection object chemical substances can be detected, so that the sensitivity of mass analysis can be improved to achieve a measurement with higher accuracy.

A chemical substance detection method according to still another aspect of the present invention includes an ion trapping step of trapping, using any one of an electric field and a magnetic field, an ion group comprising ions of a plurality of chemical substances having different masses formed by ionization; a step of applying to the ion group a SWIFT waveform which gives no voltage amplitude in a plurality of frequency bands corresponding to mass numbers of a plurality of chemical substances to remove an impurity while leaving the chemical substances; and a fragmentation step of applying energy to at least two isotopes of the chemical substances by means of a TICKLE waveform comprising frequency components corresponding to the two isotopes to fragmentate the two isotopes; and a mass analyzing step of measuring masses of the chemical substances or the fragments thereof.

In the chemical substance detection method according to the present invention, the chemical substance detection method applies a TICKLE waveform comprising frequencies corresponding to at least two isotopes of the detection object chemical substance to subject at least two isotopes of the detection object chemical substance to fragmentation, making mass analysis. Thus, a plurality of isotopes are used in the mass analysis and therefore, even when a dioxin or a precursor thereof is present in an extremely slight amount in the exhaust gas, the accuracy of detection can be improved. In addition, when used in controlling the combustion of an incineration furnace, the precision of the control can be improved.

In the chemical substance detection method, the mass analyzing step includes measuring at least two members among isotopes of fragments formed from the chemical substance.

In the chemical substance detection method according to the present invention, at least two isotopes of fragments formed from the detection object chemical substance are subjected to mass analysis. Thus, a plurality of isotopes of fragments are used in the mass analysis and therefore, even when a dioxin or a precursor thereof is present in an extremely slight amount in the exhaust gas, the accuracy of detection can be improved. In addition, when used in controlling the combustion of an incineration furnace, the precision of the control can be improved.

The chemical substance detection method further includes an ionization step of applying, before executing the ionization trap step, to the chemical substance energy higher than an ionization potential of the chemical substance and lower than a sum of the ionization potential and dissociation energy of ions of the chemical substance to ionize the chemical substance.

In the chemical substance detection method, the ionization step includes applying to the chemical substance energy higher than the ionization potential and equal to or smaller than a value of a sum of the ionization potential and 4 electron volts.

In the methods for detecting a chemical substance according to the present invention, energy higher than an ionization potential of a detection object chemical substance and lower than a sum of the ionization potential and dissociation energy of ions of the detection object chemical substance is applied to the detection object chemical substance to ionize the detection object chemical substance. Therefore, unnecessary fragments are not generated, and the detection object chemical substance to be left is allowed to remain unbroken, making it possible to improve the detection sensitivity of mass analysis. By virtue of this effect as well as the above-mentioned action and effect obtained by the chemical substance detection method, the detection sensitivity of the mass analyzer is further improved, enabling a measurement with high accuracy. In addition, the combustion of an incineration furnace can be controlled with higher precision. Further, the SWIFT voltage can be lowered, and therefore there is no need to prepare an excessively high power source and the production cost for the apparatus can be suppressed.

The other objects, features, and advantages of the present invention are specifically set forth in or will become apparent from the following detailed descriptions of the invention when read in conjunction with the accompanying drawings.

BEST MODE FOR CARRYING OUT THE INVENTION

The present invention is described in detail below with reference to the accompanying drawings. The present invention, however, is not limited to exemplary embodiments. Further, elements in the exemplary embodiments include ones that are easily conceived by persons skilled in the art or ones substantially the same. In addition, elements in the exemplary embodiments include ones that are easily conceived by persons skilled in the art.

Figure 1:
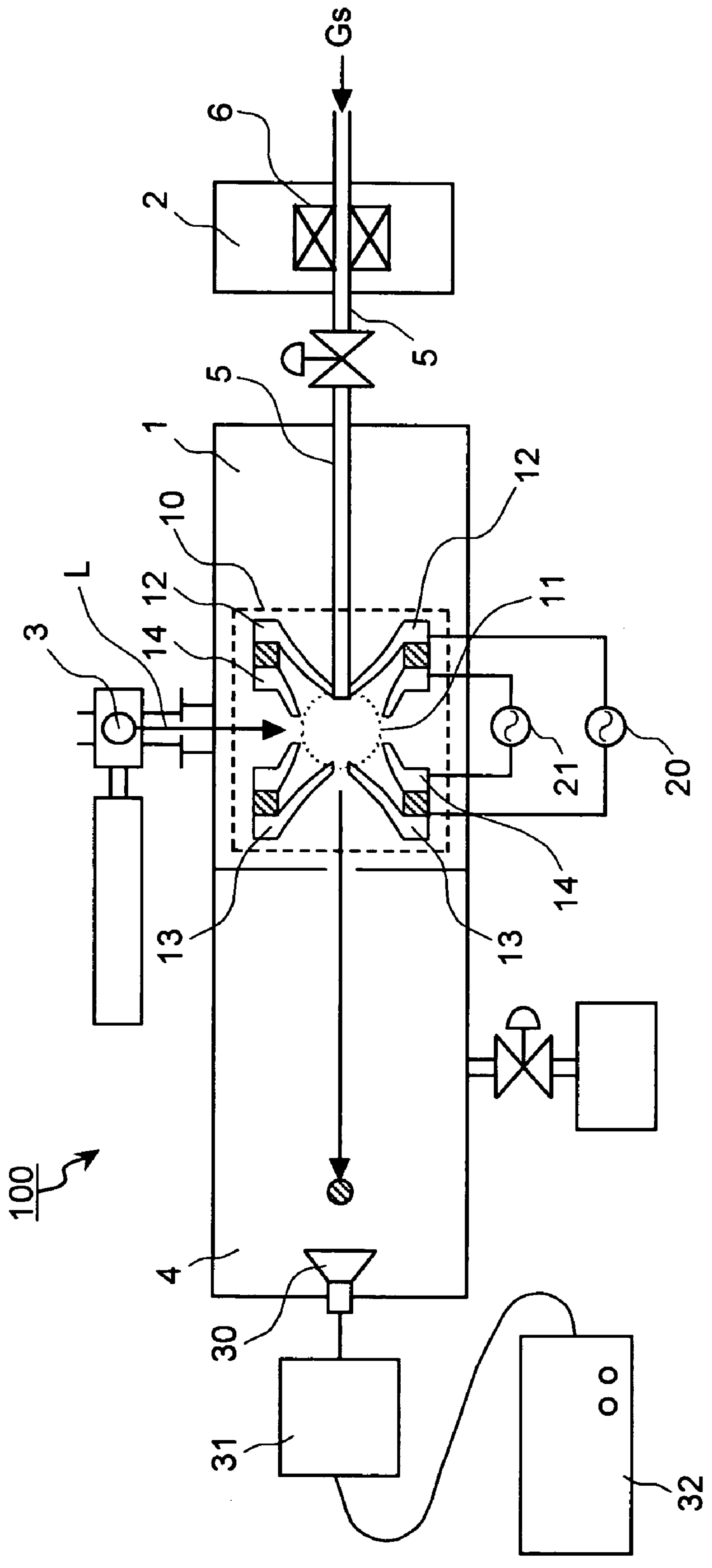
FIG. 1 is an explanatory view illustrating a chemical substance detection apparatus according to the first embodiment of the invention.

FIG. 1 is an explanatory view illustrating an chemical substance detection apparatus according to the first embodiment of the present invention. An apparatus 100 for detecting a chemical substance includes an ionization chamber 1, a gas feeding apparatus 2, a vacuum ultraviolet lamp 3 as an ionization unit, and a time-of-flight mass spectrometer 4 as a mass analyzer. The ionization chamber 1 includes, as an ion trapping unit, an RF (radio frequency) ion trapping apparatus 10 having an RF ring. The ionized detection object chemical substance in the exhaust gas is trapped in a trap 11 by means of a radio frequency electric field formed therein.

A unit that traps ions in the unit using an electric field, a magnetic field, or another electromagnetic force can be used. An electric field, a magnetic field, and other unit may be used individually or in combination appropriately. Several types of such ion trapping units are known, and, of these, preferred is the RF ion trapping apparatus 11 in which a radio frequency electric field is formed since the handling of the apparatus is relatively easy. As the ion trapping unit other than the RF type, a Penning trap employing a direct voltage and a static magnetic field can be used.

The RF ion trapping apparatus 10 as the ion trapping unit includes a first end cap 12, a second end cap 13, and an RF ring 14, and is of a three-dimensional tetrode type. As shown in FIG. 1, the RF ring 14 is disposed inside of the first end cap 12 and the second end cap 13. To the RF ring 14 is connected a radio frequency power source apparatus 21 for applying a trap voltage, which apparatus applies a radio frequency voltage as a trap voltage to the RF ring 14. The radio frequency applied traps in the trap 11 the ionized detection object chemical substance and other substances contained in the exhaust gas. An arbitrary waveform generation apparatus 20 as an arbitrary waveform generation unit is connected to each of the first and second end caps 12, 13, and applies a voltage having a specific frequency to between the end caps in the below-described SWIFT and TICKLE.

The gas feeding apparatus 2 is provided with a gas injection pipe 5, and the gas injection pipe 5 is formed from an on-off valve using an orifice, such as a pulse valve, or a capillary tube. Exhaust gas Gs from, for example, an incineration furnace, which is fed to the gas injection pipe 5, is introduced into the ionization chamber 1. A heater 6 is provided around the gas injection pipe 5. The heater 6 is a heating apparatus for preventing a detection object chemical substance from being deposited on the inner wall of the gas injection pipe 5.

The ionization chamber 1 is provided with vacuum ultraviolet lamp 3 as an ionization unit that applies energy to a detection object chemical substance to ionize it. The vacuum ultraviolet lamp 3 generates vacuum ultraviolet light L by discharge of a gas obtained by adding a rare gas, such as Ar, Kr, or Xe, or $H_2$, $O_2$, or $Cl_2$ to Ar or He. In the present embodiment, Lyman $\alpha$ light having a wavelength of 121.6 nanometers from a hydrogen plasma is used.

By changing the type of the gas discharged in the vacuum ultraviolet lamp 3, the dose of the photon energy of the vacuum ultraviolet light generated can be changed. Therefore, according to the ionization potential of a detection object chemical substance, there can be applied photon energy such that the detection object chemical substance does not undergo dissociation to an extent larger than that of the ionization potential. Thus, not only can ionization of the coexisting substance having an ionization potential higher than the photon energy be prevented, but also fragmentation of the detection object chemical substance can be suppressed.

Instead of the vacuum ultraviolet lamp 3, a laser or its harmonics can be used as the ionization unit. In this case, by using a tunable laser, a substance to be ionized can be selected by changing the photon energy generated. As the tunable laser, a conventionally known one can be used. In the present invention, a vacuum ultraviolet light having a wavelength of 50 to 200 nanometers can be used, and the wavelength of the light is more preferably 100 to 200 nanometers, desirably in the range of from 112 to 138 nanometers from the viewpoint of further suppressing the generation of unnecessary fragments.

As a unit that applies energy to a detection object chemical substance to ionize it, a laser having the wavelength of a vacuum ultraviolet light, or an excimer lamp may be used. Alternatively, ions, for example, He ions may be accelerated by means of a particle accelerator and allowed to bombard a detection object chemical substance contained in a sample gas in the ionization chamber 1. Further alternatively, electron beams are separated in terms of a sector, and a beam having energy of about 10 electron volts is taken out and allowed to bombard a detection object chemical substance contained in the exhaust gas in the ionization chamber 1.

The time-of-flight mass spectrometer 4 which is a mass analyzer specifies a detection object chemical substance by measuring its mass with respect to the ions of the detection object chemical substance contained in the exhaust gas, which ions are caused by ionization in the ionization chamber 1. By applying a drawing voltage in a pulse form to the second end cap 13 in the RF ion trapping apparatus 10, the ionized detection object chemical substance is introduced to the mass spectrometer 4 and flies in the mass spectrometer 4. The flying ions are detected by an ion detector 30, and the signal detected here is amplified by a preamplifier 31 and then taken in a data processing apparatus 32 and subjected to data processing. In the present embodiment, a microchannel plate is used in the ion detector to improve the sensitivity of ion detection. The mass spectrometer 4 measures a time of flight. There is a good correlation between a time of flight and a mass of the flying substance, and therefore a mass of the flying substance is detected from a time of flight and the substance is identified from the mass.

Figure 2:
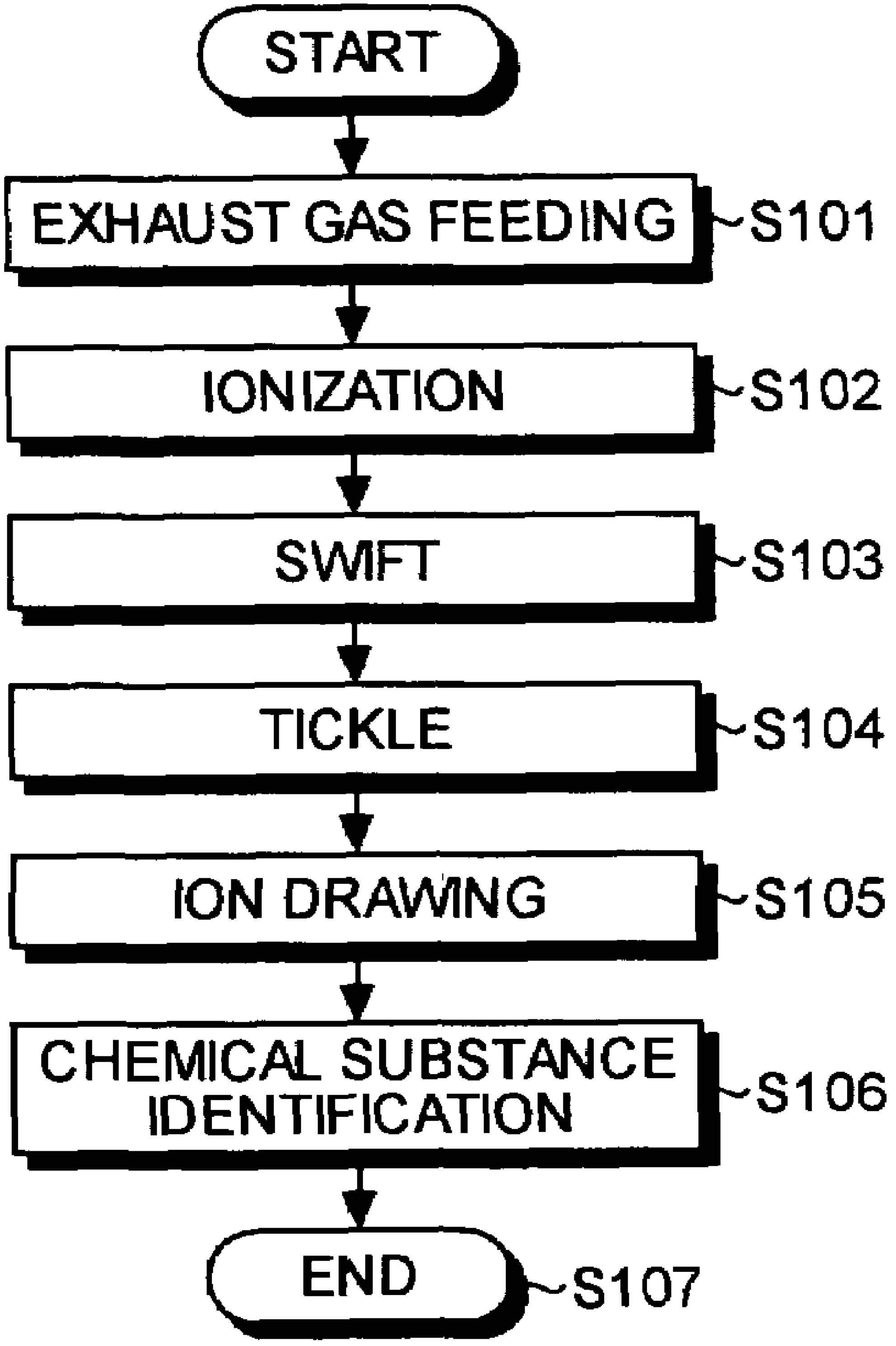
FIG. 2 is a flowchart of a chemical substance detection method according to the first embodiment of the invention.

Procedures for detecting a precursor, which is a detection object contained in the exhaust gas, using an apparatus 100 for detecting a chemical substance is described next with reference to FIG. 2. FIG. 2 is a flowchart of a chemical substance detection method according to the first embodiment of the present invention. First, exhaust gas Gs from an incineration furnace is fed to the ionization chamber 1 (step S101). Exhaust gas Gs fed to the ionization chamber 1 is then irradiated with vacuum ultraviolet light L from the vacuum ultraviolet lamp 3, so that exhaust gas Gs receives photon energy from vacuum ultraviolet light L to be ionized (step S102). The precursor as a detection object substance has an ionization potential in the range of from 8.5 to 10.0 electron volts. As mentioned above, the vacuum ultraviolet light used in the present embodiment has a wavelength of 121.6 nanometers, and its photon energy is 10.1 electron volts. Energy slightly larger than the ionization potential of the precursor is applied to the precursor, and hence the precursor can be ionized without applying thereto excess energy.

Accordingly, the ionized precursor as a detection object chemical substance can be efficiently subjected to measurement. The reason for this resides in that the ionization using a vacuum ultraviolet light generates only a very few fragments and almost all the ionized precursor can be subjected to measurement by the mass spectrometer 4. Particularly, in the exhaust gas from an incineration furnace, a precursor is present only in an extremely slight amount and therefore this effect is remarkable. In addition, the lowering of the trapping efficiency of the trap 11 can be suppressed. When fragment ions are present in a large amount, the potential created by the ions trapped in the trap 11 cancels the potential of the trap. However, the ionization using a vacuum ultraviolet light can considerably suppress generation of unnecessary fragment ions, thus making it possible to suppress a lowering of the trapping efficiency of the ion trap apparatus 11.

Further, the below-described SWIFT voltage can be lowered. The "SWIFT" means an operation for removing an impurity, in which a voltage waveform having a specific frequency is applied to between the first end cap 12 and the second end cap 13 in the trap 11 to change the orbital of ions. In an ionization method that generates many fragments, a large number of fragments having, as a parent molecule, the precursor which is a detection object chemical substance or another substance are disadvantageously generated in the mass number which should be removed in the process of SWIFT. For removing them in SWIFT, a very large voltage is required, and therefore a SWIFT voltage generation apparatus (arbitrary waveform generator) having a large power is needed. On the other hand, when the SWIFT voltage is increased, a molecule having a mass number which is not intended to be broken is broken, together with a molecule having a mass number intended to be broken, and the precursor to be left is broken, leading to a lowering of the accuracy of mass analysis.

In the ionization according to the present invention, only a very few fragments are generated, and therefore the number of fragments to be removed in the process of SWIFT is extremely small. Accordingly, the SWIFT voltage can be lowered and the precursor to be left can be allowed to remain unbroken, so that almost all the problems can be solved. When the parent molecule remaining after SWIFT is subjected to the below-described TICKLE or COOLING, fragments are generated from various parent molecules in the ionization method that generates many fragments, so that fragments of substances other than the desired precursor are contained as impurities, thus causing a lowering of the accuracy of mass analysis. By contrast, in the ionization method according to the present invention, only a few fragments are generated in the ionization, so that this problem can be substantially solved.

SWIFT is described next. This is an operation for removing unnecessary substances present in the exhaust gas while leaving a detection object chemical substance. For this operation, a voltage at a frequency in a wide band corresponding to an orbital resonance frequency of a substance to be removed is applied by an arbitrary waveform generation apparatus 20 to between the first end cap 12 and the second end cap 13 in the RF ion trapping apparatus 10. This constitutes the impurity removing unit according to the present invention. The orbital resonance frequency corresponding to the frequency of the mass number of the detection object chemical substance is excluded from the frequency in a wide band. The substance to be removed is vibrated with a large amplitude and bombards the wall of the RF ion trapping apparatus 10 to lose a charge, so that it is not present as an ion. The detection object chemical substance is still trapped in the trap 11 by the trap voltage applied to the RF ring 14. This operation is called SWIFT, and impurities can be removed while leaving the detection object chemical substance by this operation (step S103).

TICKLE is described next. TICKLE is an operation for subjecting a detection object chemical substance to fragmentation and separating the detection object chemical substance from an impurity having a mass number close to the mass number of the detection object chemical substance. Mass numbers of fragments generated from a molecule of the detection object chemical substance as a parent molecule are then measured to specify the detection object chemical substance. Further, by measuring the amount of the fragments, the concentration of the detection object chemical substance can be determined. Different from the SWIFT, in TICKLE, a voltage at a frequency corresponding to the orbital resonance frequency of the detection object chemical substance as a parent molecule is applied to between the first end cap 12 and the second end cap 13. In this case, a voltage at the frequency is applied to between the end caps by means of the arbitrary waveform generation apparatus 20. This constitutes the fragmentation unit according to the present invention. The ions of the detection object chemical substance are allowed to collide with other coexisting substances in the trap 11 to fragmentate the detection object chemical substance, thus completing the fragmentation by TICKLE (step S104).

After completion of the fragmentation by TICKLE, the application of the voltage to the RF ring 14 is terminated, and a drawing voltage in a pulse form is applied to the second end cap 13 to draw the fragment ions of the detection object chemical substance to the mass spectrometer 4 (step S105). The ions of the detection object chemical substance fly in the mass spectrometer 4 and a time of flight is measured by the mass spectrometer 4. As mentioned above, there is a good correlation between a time of flight and a mass of the flying substance, and therefore a mass of the flying substance is detected from a time of flight and the substance is identified from the mass (step S106), thus completing the measurement (step S107).

The time-of-flight mass spectrometer used in the present embodiment has advantages in that one measurement operation is completed within several tens microseconds, and the time required for measurement is very short and the response is excellent. Therefore, the mass spectrometer is preferred especially when the conditions for combustion in an actual plant are controlled in real time. As another mass analyzer, a mass analyzer of an electric field type or an RF coil type can be used. Particularly, the RF coil type can constitute a mass spectrometer having a simple structure merely by providing an ion detector at the outlet of the trap 11.

Figure 3A:
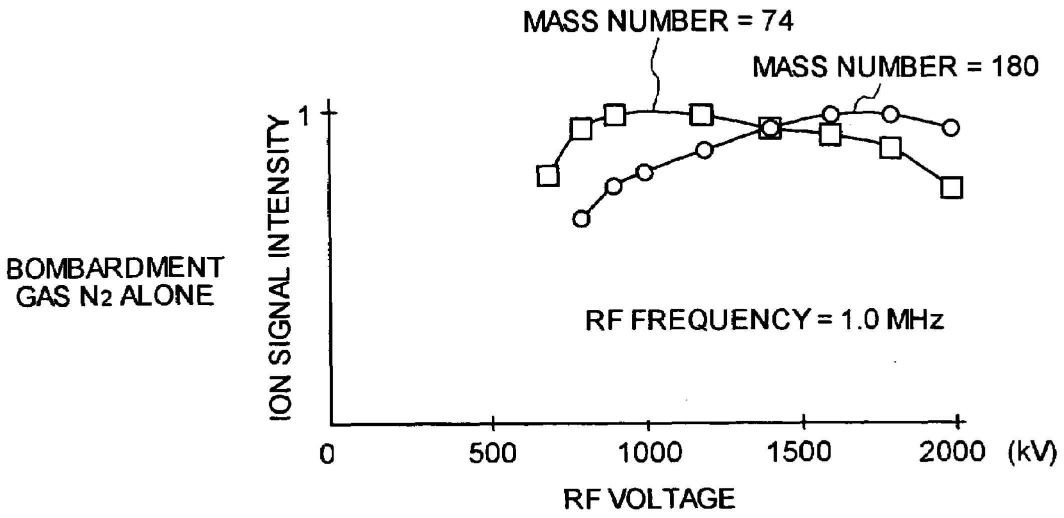
FIGS. 3A and 3B are explanatory diagrams of the ion signal intensity distributions versus the RF voltage when the trap frequency is fixed.
Figure 3B:
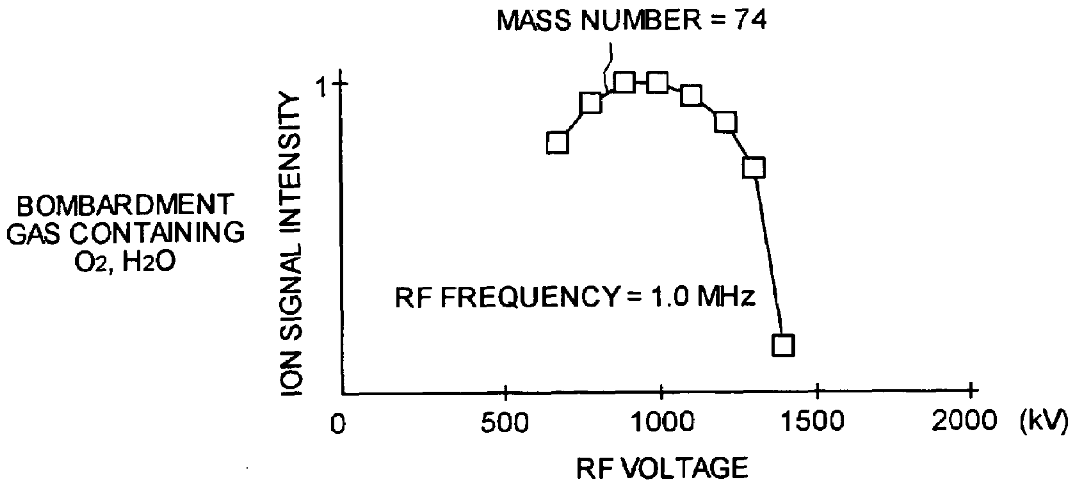
Figure 4A:
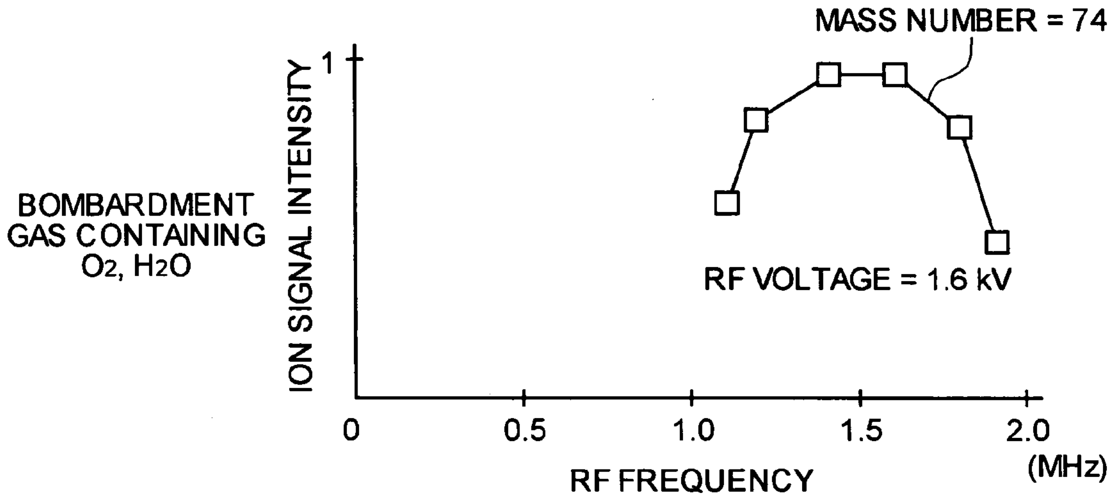
FIGS. 4A and 4B are explanatory diagrams of the ion signal intensity distributions versus the RF frequency when the RF voltage is fixed.
Figure 4B:
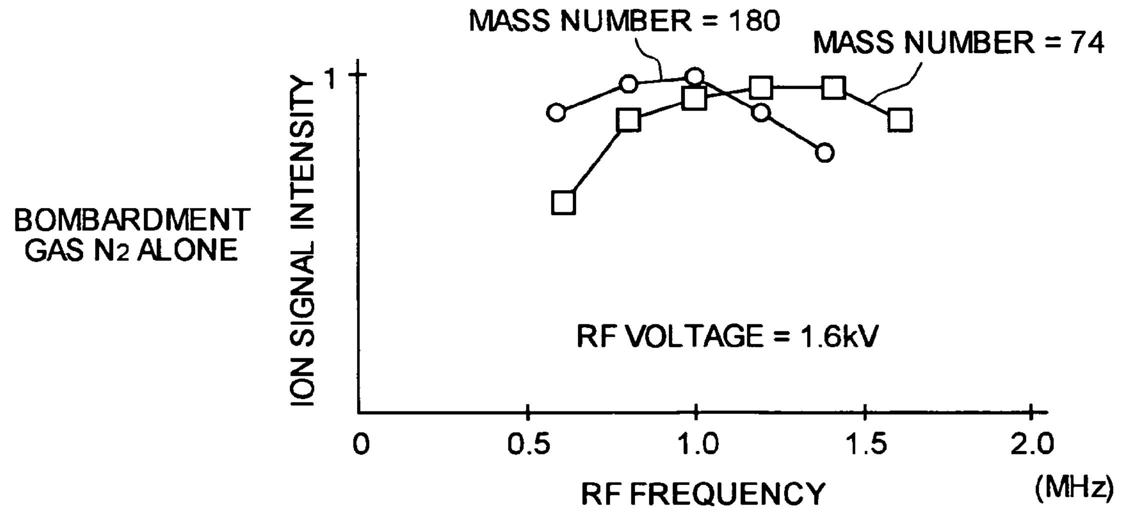

In the apparatus 100 for detecting a chemical substance according to the present invention, the exhaust gas introduced to the trap 11 is directly irradiated with vacuum ultraviolet light to ionize a substance to be measured. Ions of the substance to be measured are then subjected to fragmentation by SWIFT and TICKLE. For this reason, SWIFT or fragmentation may not be successfully achieved under the same conditions as those for the conventional ionization. The conditions for SWIFT and TICKLE are described below. FIGS. 3A and 3B are explanatory diagrams of the ion signal intensity distributions versus the RF voltage when the trap frequency is fixed. FIGS. 4A and 4B are explanatory diagrams of the ion signal intensity distributions versus the RF frequency when the RF voltage is fixed.

In the ionization conventionally used utilizing a unit other than vacuum ultraviolet light, a detection object chemical substance is ionized outside of the trap 11. For fragmentation of the detection object chemical substance, an inert gas or a bombardment gas, such as nitrogen gas, is then fed into the trap 11 from the outside to fragmentate the detection object chemical substance. Therefore, almost no air components including water vapor and oxygen contained in the exhaust gas as a gas to be measured are present in trap 11. For this reason, the ion signal intensity distributions shown in FIG. 3A and FIG. 4A are exhibited.

On the other hand, in the ionization method according to the present invention, the exhaust gas introduced to the trap 11 is directly irradiated with vacuum ultraviolet light to ionize a detection object chemical substance. Therefore, air components including water vapor and oxygen contained in the exhaust gas are present in the trap 11. When the detection object chemical substance is subjected to fragmentation by applying the below-described TICKLE voltage in an environment in which such air component molecules including water vapor and oxygen coexist with the detection object chemical substance, there may be present conditions such that fragments cannot be trapped. For example, when the RF voltage exceeds 1500 volts, fragments cannot be trapped (FIG. 3B). Further, when the RF frequency is lower than 1.0 megahertz, fragments cannot be trapped (FIG. 4B). The trap conditions mean values of the RF voltage applied to the RF ring 14 and the RF frequency. The cause of this is presumed that water vapor, i.e., a water molecule and an oxygen molecule have polarity and hence the orbital of the fragments of ions of the detection object chemical substance becomes larger, so that the ions bombard the wall of the trap 11 to lose a charge.

For trapping the fragments of ions of the detection object chemical substance even when the water molecule or oxygen molecule coexists with the substance, it is necessary to adjust the trap conditions. For example, a case is presumed in which TCB (mass numbers: 180, 182, 184) is a parent molecule, and fragments (mass numbers: 145, 147) caused by elimination of one chlorine from the parent molecule, fragments (mass numbers: 109, 111) caused by elimination of two chlorines and one hydrogen, and a fragment (mass number: 74) caused by elimination of three chlorines and one hydrogen are detected. In a conventional ionization method, when the RF voltage is 1000 to 2000 volts at an RF frequency of 1.0 megahertz, fragment ions can be advantageously trapped (see FIG. 3A).

Under the same frequency conditions in the presence of oxygen and water molecules, when the RF voltage is 700 to 1300 volts, fragment ions can be advantageously trapped, and, when the RF voltage is 900 to 1100 volts, fragment ions can be more stably trapped (see FIG. 3B). When the RF voltage is 1600 volts, an RF frequency of 1.0 megahertz is suitable in the conventional method, but, in this method, when fragment ions can be stably trapped at an RF frequency in the range of from 1.2 to 1.7 megahertz. The fragment ions can be further stably trapped at an RF frequency of 1.0 megahertz in the range of from 1.4 to 1.6 megahertz (see FIG. 4B).

In SWIFT, it is necessary to improve the trap efficiency of a substance to be measured which is a parent molecule having a higher mass, whereas, in TICKLE, it is necessary to improve the trap efficiency of the fragments of the substance to be measured having lower mass numbers. Therefore, the value of energy applied to the RF ring 14 in SWIFT, i.e., the product of an RF voltage and an RF frequency is adjusted to be larger. On the other hand, the product of an RF voltage and an RF frequency in TICKLE is adjusted to be smaller. Thus, the trap efficiency of the substance to be measured or fragments thereof in SWIFT and TICKLE can be improved.

For example, the RF frequency is fixed at 1 megahertz, and trapping is made at 1600 volts in SWIFT and at 1000 volts in TICKLE. Alternatively, the RF voltage may be fixed at 1600 volts, and trapping may be made at an RF frequency of 1.4 megahertz in SWIFT and at 1.0 megahertz in TICKLE. Further alternatively, both the RF frequency and the RF voltage may be changed. This changing may be either in a stepwise response manner or in a gradual manner. The detection object chemical substance dissipates out of the trap 11 after a predetermined time of life has lapsed, and therefore it is advantageous that the conditions are optimized so as to shorten the time required for TICKLE. Specifically, it is advantageous that the TICKLE voltage is higher.

The mass number of the detection object chemical substance after the fragmentation by TICKLE is smaller than that before the fragmentation. Therefore, it is at least necessary that the RF voltage applied to the RF ring 14 or the RF frequency after completion of TICKLE be smaller or larger than that before TICKLE. However, when the RF voltage applied to the RF ring 14 or the RF frequency is reduced or increased, the trap efficiency of the fragments having smaller mass numbers is lowered. Accordingly, when a certain period of time lapses in this state after completion of TICKLE, such fragments are reduced to lower the detection sensitivity of the mass spectrometer 4. Therefore, it is preferred to switch the conditions as mentioned above immediately after a lapse of the time needed for fragmentation of the detection object chemical substance after inputting a TICKLE waveform.

Substances other than a detection object chemical substance are removed in SWIFT, and, in this instance, an impurity having a mass number equivalent to those of the fragment ions generated in the fragmentation of the detection object chemical substance must be removed. The reason for this is that such an impurity is detected together with the fragment ions in the mass analysis after the fragmentation by TICKLE to lower the accuracy of measurement of the detection object chemical substance. In addition, when a large amount of other impurities are present in the trap 11, the trap 11 is disadvantageously saturated to lower the trap efficiency, and therefore it is advantageous that almost all the impurities are removed in SWIFT while leaving only the detection object chemical substance.

For removing all the impurities while leaving only the detection object chemical substance, a SWIFT waveform having frequency components corresponding to the mass numbers in a very wide range must be applied. However, such a SWIFT waveform having frequency components in a wide range has only small energy per unit frequency, and hence the energy which can be applied to a molecule having a certain mass number is disadvantageously small, so that the removal efficiency of impurities is lowered, thus lowering the accuracy of detection of the detection object chemical substance. Accordingly, when a SWIFT waveform having frequency components in a wide range is applied, it is necessary to improve the performance of the radio frequency generation apparatus 21 which is a SWIFT waveform source, to increase the output of an amplifier for amplifying the output of the radio frequency generation apparatus, or to expand the band of the frequency amplified, so that the size of or cost for the apparatus is disadvantageously increased.

For solving the problem, a mass spectrum is measured with respect to the impurities contained in the exhaust gas, and the impurities are removed by means of a SWIFT waveform having frequency components corresponding to the range of mass numbers which at least must be removed. The range of mass numbers which at least must be removed can be determined by, for example, letting a mass spectrum include impurities having a value of signal intensity of the mass spectrum equal to or higher than a predetermined value. The predetermined value is at least substantially equivalent to the signal intensity of the chemical substance to be measured, and it is preferred that the impurities removed are impurities having signal intensities equal to or higher than this value. The impurities removed may be impurities with further smaller mass numbers, but larger energy is required for SWIFT in such a case. Therefore, it is preferred that the impurities are impurities having signal intensities 50 percent or more of the signal intensity of the chemical substance to be measured.

In an incineration furnace as an example, the range of mass numbers which at least must be removed is, for example, 48 to 355, and impurities are removed by means of a SWIFT waveform having frequency components corresponding to this range. By this method, a measurement of a detection object chemical substance with satisfactory accuracy from a practical point of view can be achieved without applying excessively large energy to the trap 11. Thus, there is no need to use an excessively large apparatus, and the cost for the apparatus can be suppressed.

Figure 5A:
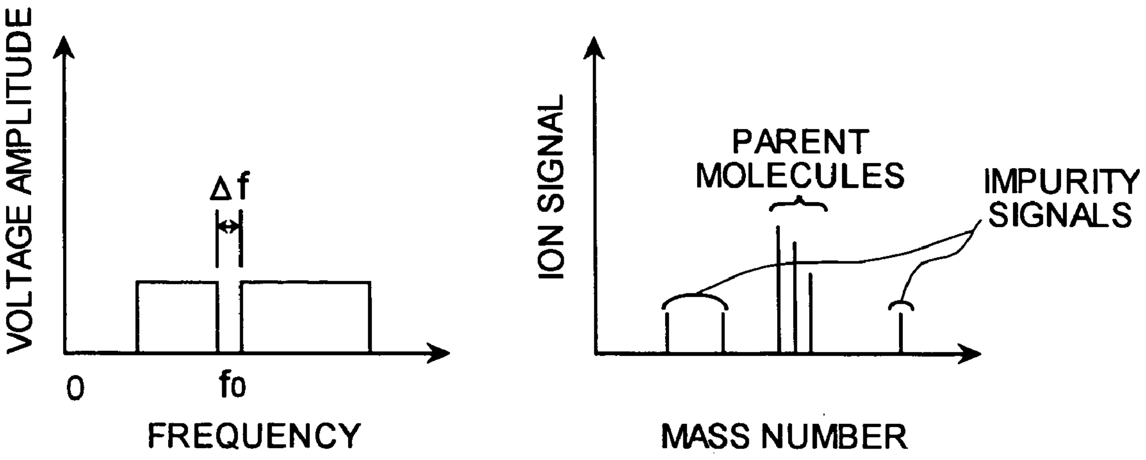
FIGS. 5A and 5B are diagrams explaining the relationship between a SWIFT frequency and an amplitude and the relationship between an ion signal and a mass number.
Figure 5B:
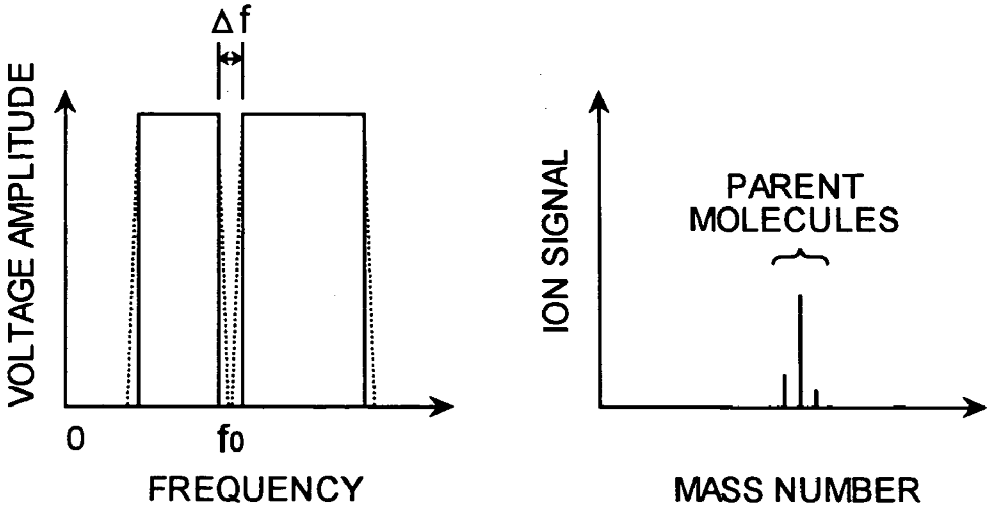
Figure 6:
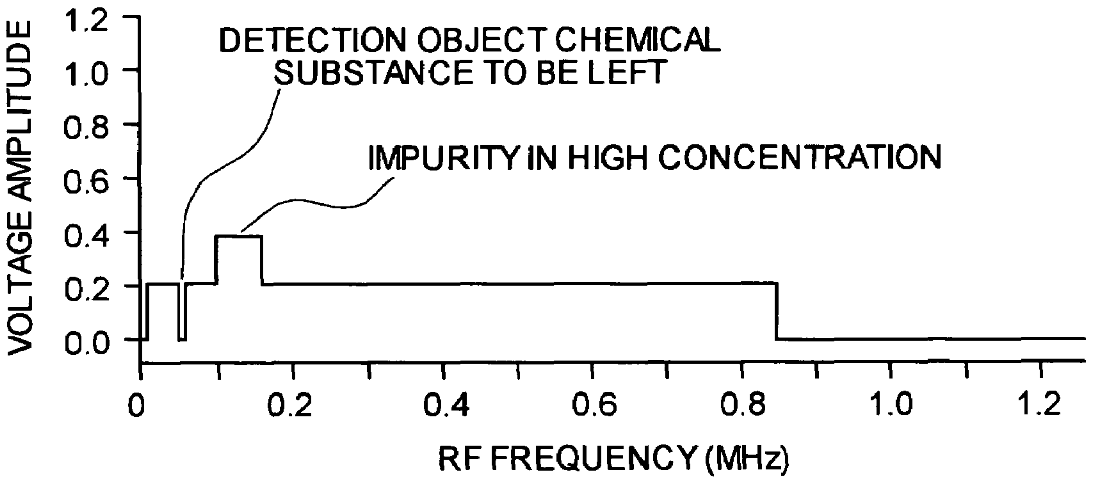
FIG. 6 is a diagram explaining a frequency spectrum of a SWIFT waveform according to the fifth embodiment of the invention.

FIGS. 5A and 5B are diagrams explaining the relationship between a SWIFT frequency and an amplitude and the relationship between an ion signal and a mass number. The mass number shown in FIGS. 5A and 5B corresponds to the SWIFT frequency in the same figure. FIG. 6 is a diagram explaining a frequency spectrum of a SWIFT waveform according to the fifth embodiment of the present invention. The frequency spectrum shows an intensity (voltage amplitude) of a SWIFT waveform or a TICKLE waveform as a function of a frequency of the SWIFT or TICKLE waveform. For removing an impurity in a very high concentration, a very high SWIFT voltage must be applied, but, in the conventional SWIFT, frequencies corresponding to all the mass numbers are applied at the same voltage amplitude. Specifically, the SWIFT voltage is determined from the voltage required for removing an impurity in the highest concentration. For this reason, when removing an impurity in a very high concentration, a very high voltage amplitude is needed as a whole, thus lowering the use efficiency of energy.

In addition, a power source apparatus having a large capacity is required, increasing the cost. Further, for leaving a parent molecule which is a detection object chemical substance, the frequency band corresponding to the mass number of the detection object chemical substance is excluded from the SWIFT waveform, but, when a high voltage amplitude is applied, the range of the mass numbers actually remaining after excluding the frequency band is smaller than intended, so that part of the detection object chemical substance is removed, causing a problem in that the detection accuracy is lowered. The reason for this resides in that the actual frequency spectrum of a SWIFT waveform is not an ideal rectangular form indicated by the solid line shown in FIG. 5A but a rectangular form which slightly broadens toward the bottom indicated by the broken line shown in FIG. 5B. Specifically, the frequency spectrum of a SWIFT waveform is actually in a rectangular form which broadens toward the bottom, and therefore the frequency band corresponding to the mass number of the detection object chemical substance indicated by AF shown in the figures becomes narrower, so that the detection accuracy is lowered.

Therefore, as shown in FIG. 6, the voltage amplitude of the SWIFT waveform having a frequency corresponding to the mass number of an impurity in a high concentration is increased and the voltage amplitude for the portion of an impurity in a low concentration is lowered. Thus, an impurity in an especially high concentration can be selectively removed. It is preferred that the impurity of which the voltage amplitude of a SWIFT waveform is increased is an impurity having a signal intensity at least equivalent to the signal intensity of a chemical substance to be measured. The impurity may be an impurity present in a further smaller mass number, but larger energy is required for SWIFT in such a case. Therefore, it is preferred that the impurity is an impurity having a signal intensity 50 percent or more of the signal intensity of the chemical substance to be measured. Thus, the voltage amplitude of the SWIFT waveform can be lowered as a whole, so that an impurity can be removed with increased use efficiency of energy. In addition, a power source apparatus having a small capacity can be used, and hence the power source apparatus can be reduced in size and the cost can be lowered. Further, the detection object chemical substance can be surely left in the SWIFT operation, thus making it possible to improve the detection accuracy of the mass spectrometer 4.

Figure 7A:
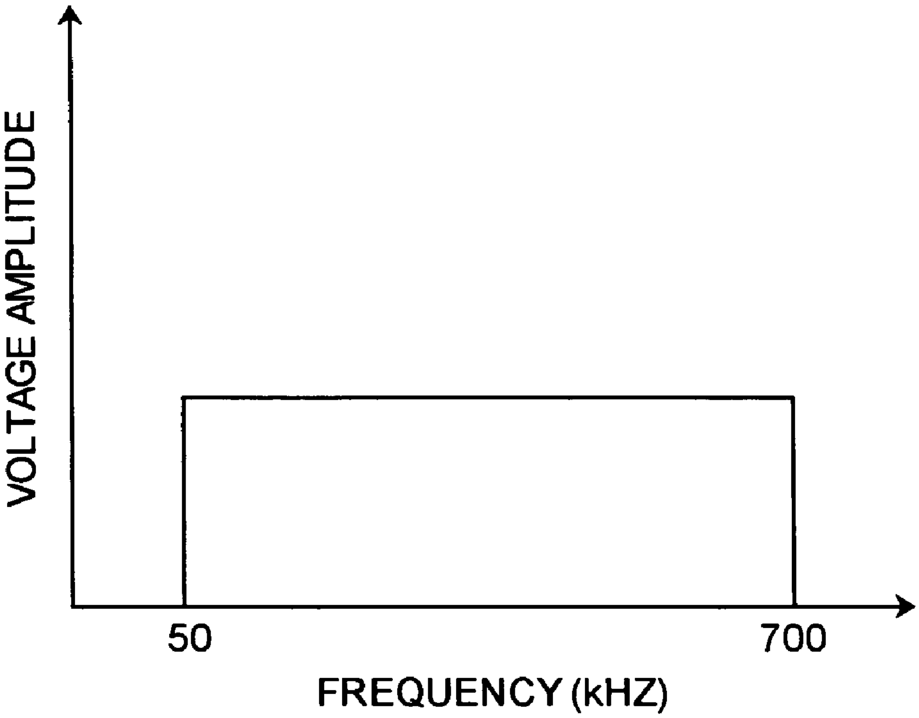
FIGS. 7A and 7B are diagrams explaining a frequency spectrum of a conventional SWIFT waveform.
Figure 8A:
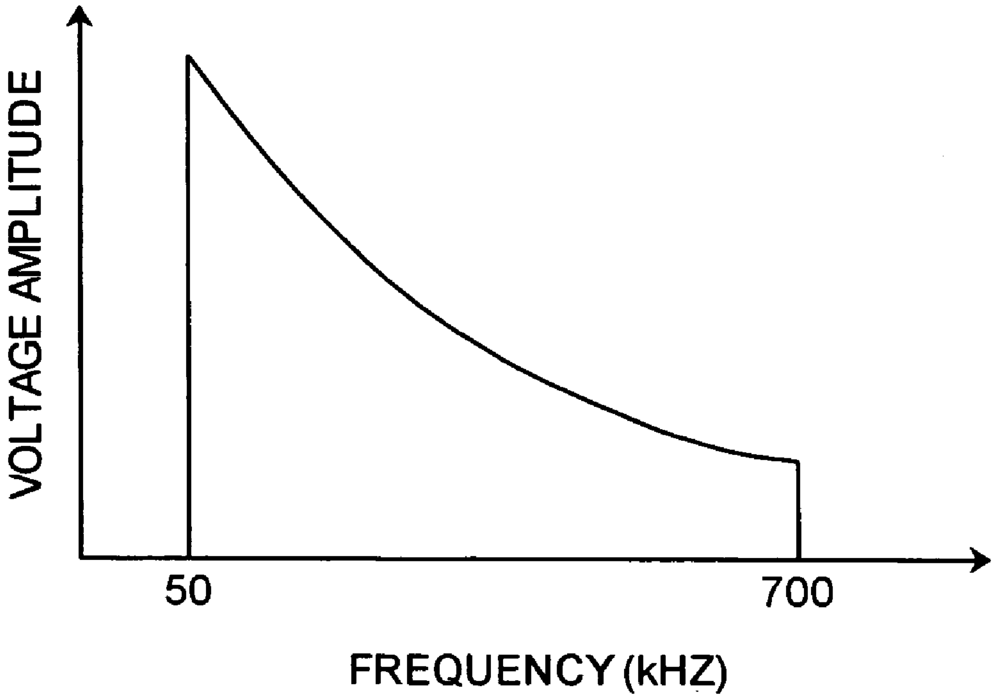
FIGS. 8A and 8B are diagrams explaining a frequency spectrum of a SWIFT waveform according to the sixth embodiment of the invention.
Figure 8B:
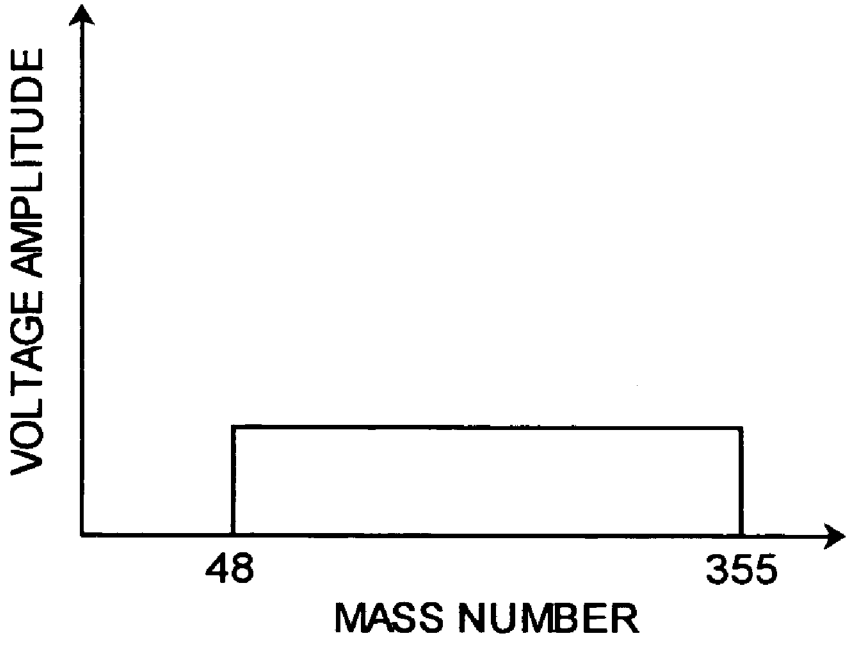

FIGS. 3A and 3B are diagrams explaining a frequency spectrum of a conventional SWIFT waveform. FIGS. 8A and 8B are diagrams explaining a frequency spectrum of a SWIFT waveform according to the sixth embodiment of the present invention. FIGS. 7A and 8B are individually obtained by converting the frequency spectrum of a SWIFT waveform so that the mass number is taken as an abscissa, namely, a diagram as a function of the mass number. A general SWIFT waveform is formed by subjecting to inverse Fourier transform a rectangular-form frequency spectrum of which the amplitude is not changed even when the resonance frequency of ions becomes larger (FIG. 7A). The SWIFT waveform in this case is a waveform on which the resonance frequency corresponding to the mass number of an impurity to be removed superpose. This waveform is ideally a continuous waveform including whole of the orbital resonance frequencies corresponding to a certain mass range. However, the actual inverse Fourier transform is made based on data of limited resonance frequencies, and the resultant SWIFT waveform includes discrete frequency components and the frequency pitch is constant. When this waveform is represented in terms of a mass number, the frequency pitch is larger in a region in which the mass number is large, and the frequency pitch is smaller in a region in which the mass number is small.

Figure 7B:
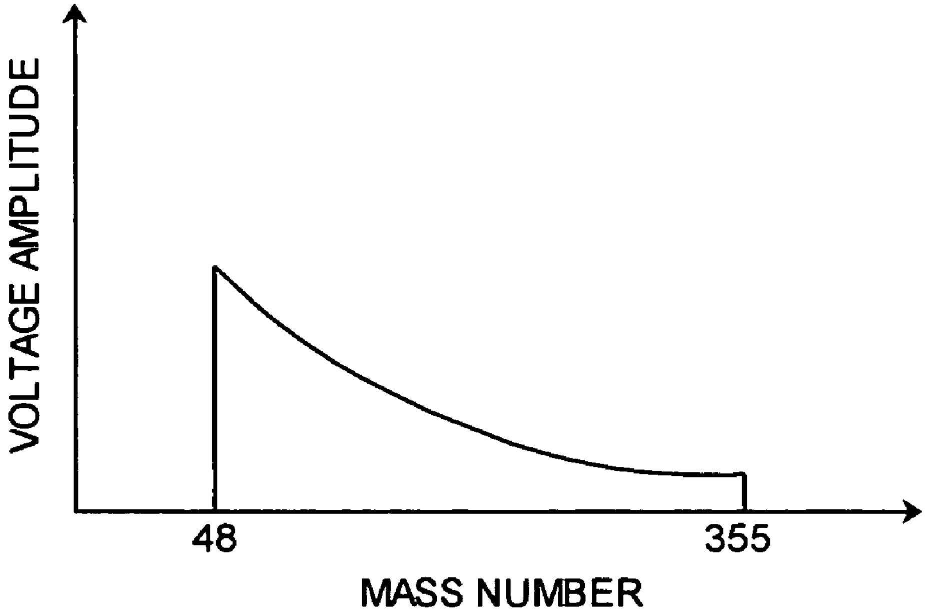

When using such a SWIFT waveform, an amplitude at a high energy density is applied to an ion having a smaller mass number, but an amplitude at only a low energy density is applied to an ion having a larger mass number (FIG. 7B). For this reason, an ion having a smaller mass number can be easily broken, but an ion having a larger mass number is difficult to be broken, and thus it is left as an impurity. Unnecessary fragments are generated by TICKLE to lower the accuracy of mass analysis.

For solving this problem, a SWIFT waveform formed by subjecting to inverse Fourier transform a frequency spectrum in which the voltage amplitude is reduced as the resonance frequency corresponding to the mass number of an ion becomes higher is used (FIG. 8A). By using such a SWIFT waveform, satisfactory energy can be also applied to an ion having a larger mass number (FIG. 8B). Specifically, there can be applied a SWIFT waveform in which the voltage amplitude has a fixed distribution, irrespective of the mass number of a molecule to be removed by SWIFT (FIG. 8B), so that even an ion having a larger mass number can be further surely removed. Further, required and satisfactory energy can be applied to an ion having a smaller mass number, so that the use efficiency of energy can be improved. In addition, an excessively large power source apparatus is not required, and therefore the cost for the apparatus can be suppressed.

Figure 9:
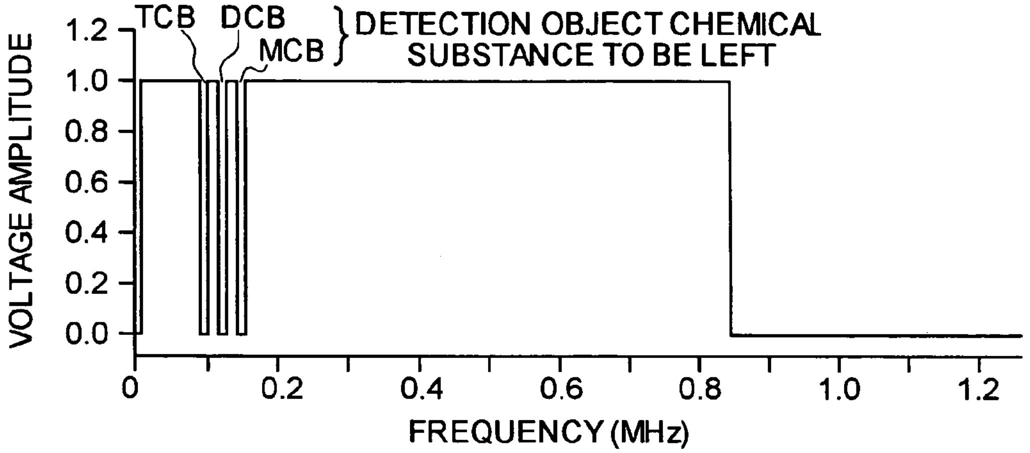
FIG. 9 is a diagram explaining a frequency spectrum of a SWIFT waveform according to the seventh embodiment of the invention.
Figure 10A:
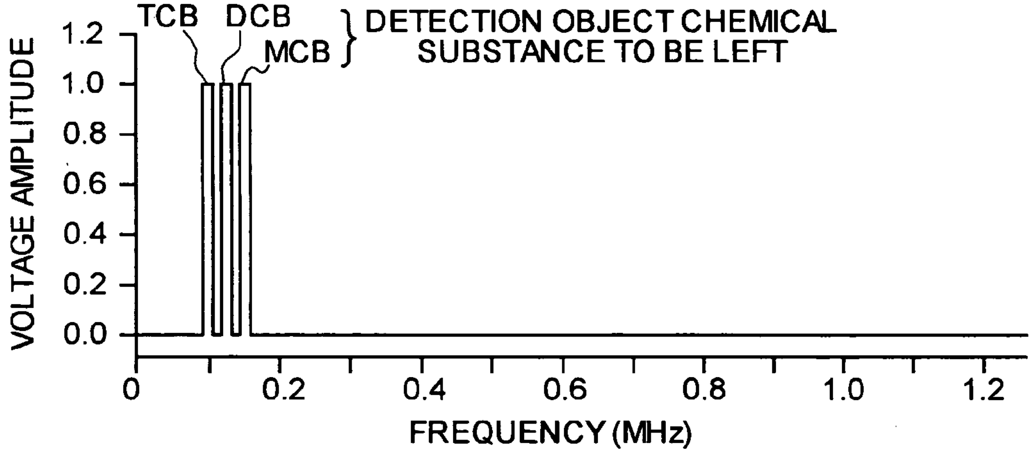
FIGS. 10A and 10B are diagrams explaining a frequency spectrum of a TICKLE waveform according to the seventh embodiment of the invention.
Figure 10B:
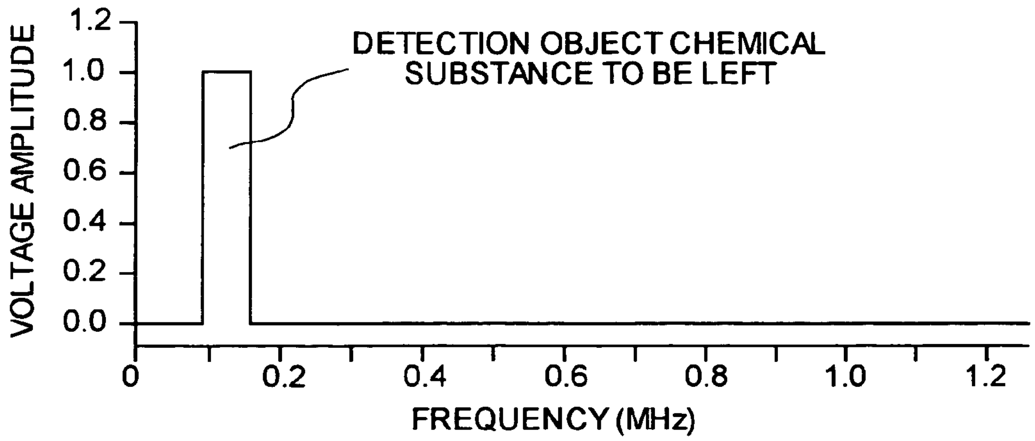

FIG. 9 is a diagram explaining a frequency spectrum of a SWIFT waveform according to the seventh embodiment of the present invention. FIGS. 10A and 10B are diagrams explaining a frequency spectrum of a TICKLE waveform according to the seventh embodiment of the present invention. In the measurement by means of the apparatus 100 for detecting a chemical substance with respect to a detection object chemical substance which is, for example, a precursor of a dioxin, when a plurality of detection object chemical substances are simultaneously subjected to measurement, the detection accuracy can be further improved. Particularly, the amount of the precursor of a dioxin contained in the exhaust gas from an incineration furnace is extremely slight, and hence an improvement of the detection accuracy is very important when the conditions for combustion of the incineration furnace are controlled in real time.

For subjecting a plurality of detection object chemical substances to measurement simultaneously, there is used in SWIFT a frequency spectrum of a SWIFT waveform in which the voltage amplitude is 0, that is, a SWIFT waveform which gives no voltage amplitude in the resonance frequency band corresponding to the mass numbers of the detection object chemical substances (FIG. 9). The frequency spectrum of this SWIFT waveform is then subjected to inverse Fourier transform to form a SWIFT waveform. When SWIFT is conducted using the SWIFT waveform obtained by the inverse transform, the detection object chemical substances are still trapped in the trap 11 of ion trapping apparatus 10, and therefore they can be separated from impurities.

The detection object chemical substances are then subjected to fragmentation by means of a TICKLE waveform formed by subjecting to inverse Fourier transform a TICKLE frequency spectrum having a larger amplitude in the frequency band corresponding to the mass numbers of the detection object chemical substances (FIG. 10A). The resultant fragment ions of the detection object chemical substances are then measured by means of the mass spectrometer 4 (see FIG. 1) to identify the detection object chemical substances, so that their concentrations can be determined. Alternatively, TICKLE may be conducted using a TICKLE waveform formed by subjecting to inverse Fourier transform a TICKLE frequency spectrum having a large amplitude in the range encompassing whole of the frequencies corresponding to the mass numbers of the detection object chemical substances (FIG. 10B). Further alternatively, the frequencies corresponding to the mass numbers of the detection object chemical substances may be individually applied to the respective substances successively.

As described above, when a plurality of detection object chemical substances are simultaneously subjected to measurement, the detection accuracy can be advantageously improved. However, when the plurality of detection objects chemical substances are simultaneously subjected to measurement, the following problem arises. For example, a case is considered in which a fragment pattern having TCB (trichlorobenzene) and DCB (dichlorobenzene) as parent molecules is obtained at the same time. A difference between a mass number of 145 of the TCB fragment and a mass number of 146 of the DCB fragment is as small as 1. Therefore, when TCB and DCB are simultaneously subjected to TICKLE, part of the TCB fragment may be broken by the near TICKLE frequency of DCB. In such a case, for example, a concentration of TCB cannot be determined by subjecting TCB to fragmentation and separating TCB from an impurity having a mass number equivalent to the mass number of TCB to measure a signal of the fragment, so that the accuracy of detection of TCB is lowered. Thus, in the TICKLE according to the seventh embodiment, various cares should be taken for accurately applying a frequency corresponding to the mass number or optimizing the TICKLE voltage. In addition, even when such cares are taken, the fragmentation may not be appropriately achieved.

For solving the problem, in the present embodiment, a detection object chemical substance having a smaller mass number is first subjected to fragmentation by TICKLE, and another detection object chemical substance or an impurity in the range of the mass number of the detection object chemical substance is removed. A detection object chemical substance having a larger mass number is subjected to TICKLE to generate a fragment of the detection object chemical substance having a larger mass number in the range of the mass number in which the detection object chemical substance having a smaller mass number is present.

By this method, when the detection object chemical substance having a larger mass number is subjected to fragmentation, the detection object chemical substance having a smaller mass number has already been subjected to fragmentation, preventing the fragment of the detection object chemical substance having a larger mass number from being broken by the TICKLE for the detection object chemical substance having a smaller mass number. Accordingly, even when a plurality of detection object chemical substances having different mass numbers are detected simultaneously, a measurement with high accuracy can be achieved.

Specifically, a case is considered in which TCB (mass numbers: 180, 182, 184, 186), DCB (mass numbers: 146, 148, 150), and MCB (monochlorobenzene; mass numbers: 112, 114) are detected simultaneously. Prior to TICKLE, impurities are removed by SWIFT while leaving these detection object chemical substances. For subjecting MCB to fragmentation, a TICKLE frequency corresponding to the mass number of MCB is then applied to first and second end caps 12 and 13 to generate a fragment having a mass number of 77. In this case, substances having mass numbers of 112 to 114 are not present in the trap 11 of the ion trapping apparatus 10.

After the fragmentation of MCB, DCB is subjected to fragmentation by applying a TICKLE frequency corresponding to the mass number of DCB. The resultant fragments include ones having mass numbers of 111 and 113 caused by elimination of one chlorine from DCB and one having a mass number of 75 caused by elimination of two chlorines and one hydrogen. Finally, TCB is subjected to fragmentation by applying a frequency corresponding to the mass number of TCB. The fragments generated in this instance include ones having mass numbers of 145, 147, and 149 caused by elimination of one chlorine, ones having mass numbers of 109 and 111 caused by elimination of two chlorines and one hydrogen, and one having a mass number of 74 caused by elimination of three chlorines and one hydrogen. The corresponding TICKLE frequencies are successively applied, respectively, to the fragments at certain intervals.

After completion of the fragmentation of the detection object chemical substances, the fragment ions in the trap 11 are subjected to Cooling without applying a voltage to between the first and second end caps 12, 13 in the ion trapping apparatus 10. The Cooling unit that the fragment ions collide with neutral gas in the trap 11 to lose their energy, and the fragment ions are cooled by this procedure.

The Cooling can improve the accuracy of mass measurement by the mass spectrometer 4.

After completion of Cooling, a drawing voltage is applied to the second end cap 13 to introduce the fragments to the mass spectrometer 4 and the masses of the fragments introduced are measured, so that the concentrations of the detection object chemical substances can be determined. Specifically, the concentrations of MCB and DCB can be determined by selecting, respectively, the signal intensity of a fragment having a mass number of 77 and the signal intensities of fragments having mass numbers of 113 and 75. The concentration of TCB can be determined by selecting the signal intensity of a fragment having a mass number which does not overlap the fragments of MCB and DCB, for example, a mass number of 145, 147, 149, 109, or 74.

Detection object chemical substances from which fragments generated have mass numbers which do not overlap, for example, TCB and TCP can be simultaneously broken by means of a TICKLE waveform. For example, MCB and MCP are first subjected to fragmentation, and then DCB and DCP, and finally TCB and TCP are subjected to fragmentation, enabling a simultaneous measurement of six types of detection object chemical substances. In this case, fragmentation is conducted two substances by two substances, and hence the time required for the fragmentation is only about three times the time required for fragmentation for six types of substances conducted one substance by one substance.

A detection object chemical substance may have an isotope, and such a detection object chemical substance has different mass numbers. For example, MCB has isotopes having mass numbers of 112 and 114. The reason for this is that the chlorine bonded to a benzene ring is of two types having mass numbers of 35 and 37. In such a detection object chemical substance having isotopes, the density of the detection object chemical substance having one mass number is lower than the collective density of the detection object chemical substance, and therefore, when a substance having one mass number is solely subjected to measurement by means of mass spectrometer 4, the sensitivity of measurement is disadvantageously lowered.

Taking the MCB as an example, when MCB having a mass number of 112 is solely subjected to measurement, MCB having a mass number of 114 is not measured, so that the concentration actually detected is lower than the collective concentration of MCB by the concentration of MCB having a mass number of 114 which is not measured. Particularly, a precursor of a dioxin contained in the exhaust gas from an incineration furnace, which is a detection object chemical substance, has an extremely low concentration, and therefore it is necessary to improve the detection sensitivity as high as possible.

Figure 11A:
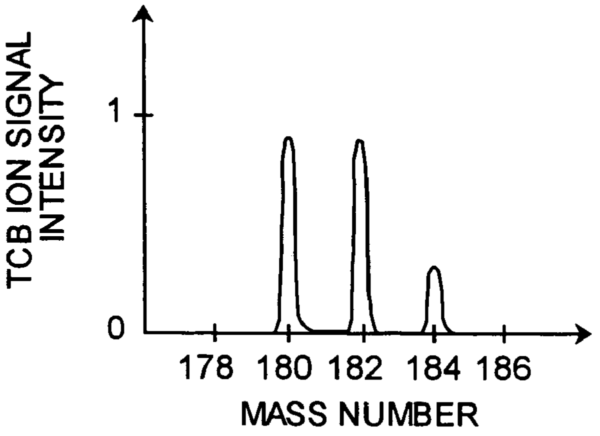
FIGS. 11A to 11D are diagrams explaining a frequency spectrum of a TICKLE waveform according to the ninth embodiment of the invention wherein the diagrams are individually obtained by converting the frequency spectrum so that the mass number is taken as an abscissa.

By subjecting to fragmentation all of the isotopes of at least two detection object chemical substances, the problem of a lowering of the measurement sensitivity can be solved. An explanation is made below, with taking the isotopes of TCB as an example, but the present invention is not limited to TCB, and any detection object chemical substances can be applied as long as they have isotopes. FIGS. 11A to 11D are diagrams explaining a frequency spectrum of a TICKLE waveform according to the ninth embodiment of the present invention wherein the diagrams are individually obtained by converting the frequency spectrum so that the mass number is taken as an abscissa. FIG. 11A shows the distribution of isotopes in TCB ions.

Figure 11B:
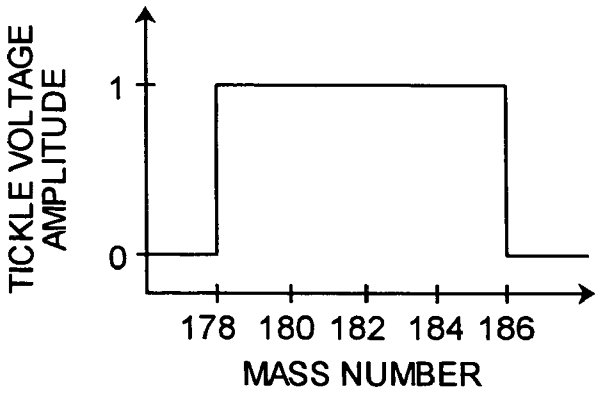
Figure 11C:
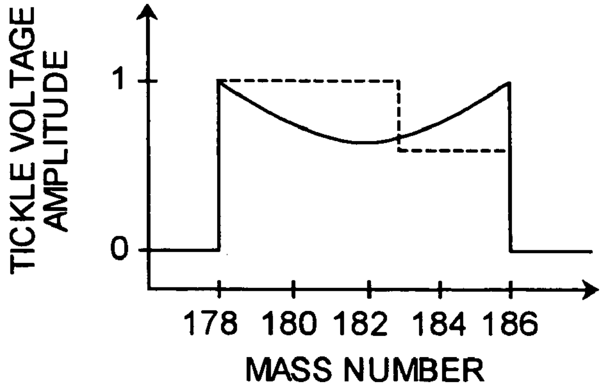

For example, all the isotopes of detection object chemical substances can be subjected to fragmentation, an isotope having a theoretically lower concentration can be removed from all the isotopes, or the isotopes of detection object chemical substances from which the mass number having a larger impurity ratio is excluded can be subjected to fragmentation. In this case, as a TICKLE waveform, there can be used one obtained by subjecting to inverse Fourier transform a frequency spectrum which gives a large amplitude in a wide range of a resonance frequency band so as to include the mass numbers of all the isotopes of at least two detection object chemical substances (FIG. 11B).

The mass number of which the resonance frequency affects ions has variation and therefore, when a frequency spectrum having a fixed amplitude is used, a phenomenon occurs in which TICKLE is difficult for the isotopes having the maximum and minimum mass numbers and TICKLE is relatively easy for the isotope having an intermediate mass number. For this reason, when using a frequency spectrum in which the voltage amplitude is large in the maximum and minimum mass numbers of the isotopes of the detection object chemical substance, all of the plurality of isotopes as the object of TICKLE can be subjected to substantially the same TICKLE, thus enabling substantially uniform fragmentation. Alternatively, there may be used a frequency spectrum in which the voltage amplitude is large in the maximum and minimum mass numbers of the isotopes as the object of fragmentation and the voltage amplitude is relatively small in the intermediate mass number (solid line in FIG. 11C). Further alternatively, there may be used a frequency spectrum in which the voltage amplitude in the isotope having a relatively low ion signal intensity is smaller than the voltage amplitude in the isotope having a relatively high ion signal intensity (broken line in FIG. 11C).

Figure 11D:
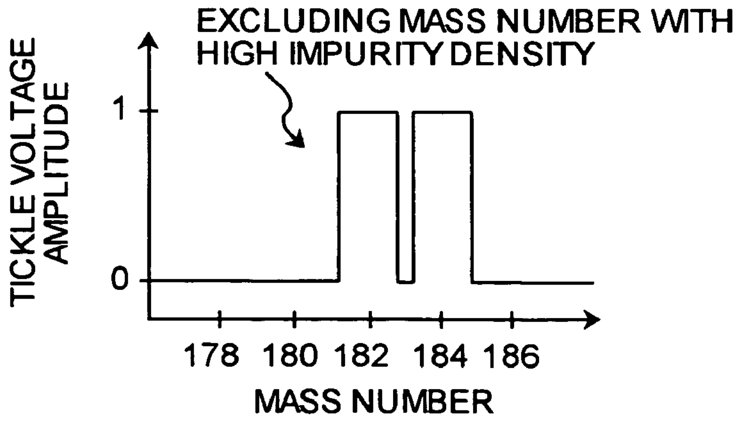

On the other hand, a large amount of impurities having substantially the same mass number as that of one certain isotope may be present. For example, it is presumed that, in FIG. 11D, a large amount of impurities having the same mass number as that of a TCB isotope having a mass number of 180 are present. In such a case, a plurality of isotopes excluding this isotope may be subjected to fragmentation so that the large amount of impurities are not subjected to fragmentation, achieving a measurement with high accuracy. In this case, there can be used a TICKLE waveform obtained by subjecting to inverse Fourier transform a frequency spectrum comprising a plurality of resonance frequencies corresponding to the mass numbers of a plurality of isotopes which do not contain impurities very much in the same mass number and which are selected from the isotopes (isotopes of TCB here) (FIG. 11D).

A detection object chemical substance has an isotope, and a fragment of the detection object chemical substance has an isotope similarly. Therefore, a measurement of the fragment has similar problems described in connection with the eighth embodiment. Conventionally, the concentration of a detection object chemical substance has been measured only from one fragment, or the concentration of a detection object chemical substance has been estimated by pattern matching of fragments.

However, in a substance present only in an extremely low concentration, such as a precursor of a dioxin contained in the exhaust gas from an incineration furnace, when one isotope of a fragment is merely measured, a measurement with satisfactory sensitivity cannot be made. Even in the pattern matching of a plurality of fragments, the absolute number of the fragments in one isotope is too small and unsatisfactory for statistically estimating the concentration.

For solving the problem, among the isotopes of the fragments formed from a detection object chemical substance, at least two isotopes are subjected to measurement.

Specifically, in a spectrum (signal voltage) of a certain fragment, a value of a sum of maximum values of the spectrum of a plurality of isotopes, or a value of a sum of areas of the spectrum of a plurality of isotopes is used as a measurement value of mass spectrometer 4. By this method, all the isotopes of a certain fragment can be used, and therefore, even when the concentration of a substance to be measured is extremely low, the sensitivity of measurement by mass spectrometer 4 can be improved. In addition, when a spectrum having a large noise component is present, for example, an impurity fragment appears in the mass number of a certain isotope, the mass number of the isotope excluding the spectrum of the isotope may be selected to determine the concentration of the substance to be measured, so that the noise of an impurity can be removed, thus enabling a measurement with higher accuracy.

As described above, in the chemical substance detection apparatus according to the present invention, in ionization of a detection object chemical substance, energy higher than an ionization potential of the detection object chemical substance and lower than a sum of the ionization potential and dissociation energy of ions of the detection object chemical substance is applied to the detection object chemical substance. Therefore, the detection object chemical substance can be ionized without being broken, and further, generation of unnecessary fragments, which is a problem caused when removing an impurity by SWIFT, can be considerably suppressed. Accordingly, the detection object chemical substance to be left is allowed to remain unbroken, making it possible to improve the detection sensitivity of the mass analyzer. Further, a SWIFT waveform is merely applied for removing an impurity and hence, the impurity can be quickly removed. Thus, the rate of detection of the detection object chemical substance can be increased and hence it is preferred in the control of an actual incineration furnace.

In the chemical substance detection apparatus according to the present invention, fragmentation of the detection object chemical substance is performed by means of a fragmentation unit that applies a TICKLE waveform. Therefore, even when an impurity is present in a frequency band corresponding to the mass number of the detection object chemical substance, the effect of the impurity can be removed to achieve an accurate measurement. In addition, only a very few fragments are generated in the ionization and therefore, in the fragmentation of the detection object chemical substance, the desired detection object chemical substance can be efficiently subjected to fragmentation. Accordingly, the detection sensitivity of the mass analyzer can be improved, and the combustion can be controlled with higher precision.

In the chemical substance detection apparatus according to the present invention, the energy applied to the detection object chemical substance by the ionization unit is higher than the ionization potential and equal to or smaller than a value of a sum of the ionization potential and 4 electron volts. When the detection object chemical substance is ionized by energy of light, the wavelength of the light is 50 to 200 nanometers. Therefore, an impurity can be removed without generating unnecessary fragments. In addition, a vacuum ultraviolet lamp is used for such light, and hence the handling is easy and the construction of the apparatus can be simplified.

In the chemical substance detection apparatus according to the present invention, the voltage amplitude of a SWIFT waveform in a frequency corresponding to the mass number of an impurity present in a high concentration such that it exhibits a signal intensity higher than a specific signal intensity is increased, and the voltage amplitude for an impurity in a low concentration is lowered. Therefore, an impurity in an especially high concentration can be selectively removed. An impurity can be selectively removed and hence only small energy is required for SWIFT. Thus, a power source apparatus can be reduced in size, and there is no need to use an excessively high power source and this is advantageous from an economical point of view.

In the chemical substance detection apparatus according to the present invention, the energy applied to an impurity having a larger mass number is higher than the energy applied to an impurity having a smaller mass number. Further, the chemical substance detection apparatus according to the present invention is such that, when the frequency spectrum of a SWIFT waveform in which the voltage amplitude is increased as the frequency is smaller is converted so that the mass number is taken as an abscissa, the voltage amplitude per unit mass number is a substantially fixed value. Therefore, satisfactory energy is applied to an impurity having a larger mass number to remove it and energy in a required and satisfactory range can be applied to ions having small mass numbers, and thus the use efficiency of the energy can be improved, so that an excessively high power source apparatus is not required and hence the cost for the apparatus can be suppressed.

In the chemical substance detection apparatus according to the present invention, an impurity is removed using a SWIFT waveform which gives no voltage amplitude in the frequency bands corresponding to a plurality of detection object chemical substances. In addition, the detection object chemical substances are detected simultaneously by the mass analyzer. Thus, a plurality of detection object chemical substances are detected simultaneously and therefore, a measurement with high accuracy can be achieved and the precision of the combustion control can be improved.

In the chemical substance detection apparatus according to the present invention, the chemical substance detection apparatus further includes an ionization unit that applies to the detection object chemical substance energy higher than an ionization potential of the detection object chemical substance and lower than a sum of the ionization potential and dissociation energy of ions of the detection object chemical substance to ionize the detection object chemical substance. In the chemical substance detection apparatus according to the present invention, the ionization unit in the chemical substance detection apparatus applies to the detection object chemical substance energy higher than the ionization potential and equal to or smaller than a value of a sum of the ionization potential and 4 electron volts. In these apparatuses for detecting a chemical substance according to the present invention, energy higher than the ionization potential of the detection object chemical substance and lower than a sum of the ionization potential and dissociation energy of ions of the detection object chemical substance is applied to the detection object chemical substance to ionize the detection object chemical substance. Therefore, unnecessary fragments are not generated, and the detection object chemical substance to be left is allowed to remain unbroken, making it possible to improve the detection sensitivity of the mass analyzer. By virtue of this effect as well as the above-mentioned action and effect obtained by the chemical substance detection apparatus, the detection sensitivity of the mass analyzer is further improved, enabling a measurement with high accuracy.

In the chemical substance detection method according to the present invention, in ionization, energy higher than an ionization potential of a detection object chemical substance and lower than a sum of the ionization potential and dissociation energy of ions of the detection object chemical substance is applied to the detection object chemical substance. Therefore, the detection object chemical substance can be ionized without being broken, and further, generation of unnecessary fragments can be considerably suppressed in the ionization. Accordingly, the detection object chemical substance to be left can be allowed to remain unbroken, making it possible to improve the detection sensitivity of the mass analyzer.

In the chemical substance detection method according to the present invention, fragmentation of the detection object chemical substance is conducted by applying a TICKLE waveform to the detection object chemical substance. Therefore, even when an impurity is present in a frequency band corresponding to the mass number of the detection object chemical substance, the effect of the impurity can be removed to achieve an accurate measurement. Accordingly, almost all the fragments of the detection object chemical substance can be subjected to mass analysis, so that the detection sensitivity of analysis in the mass analyzing step can be improved.

In the chemical substance detection method according to the present invention, an impurity present in a predetermined ratio or more is selectively removed. Therefore, the energy needed for removing the impurity in a required and satisfactory amount is small, as compared to the energy needed for removing all the impurities. Only small energy is needed, and hence a power source apparatus can be reduced in size and this is advantageous from an economical point of view.

In the chemical substance detection method according to the present invention, the voltage amplitude of a SWIFT waveform in a frequency corresponding to an impurity having a signal intensity higher than a specific signal intensity is increased, and the voltage amplitude in a frequency corresponding to an impurity in a low concentration is lowered. Therefore, an impurity in an especially high concentration can be selectively removed, and the energy required for removing an impurity in a low concentration can be reduced. Thus, only small energy is required for removing an impurity, and there is no need to use an excessively high power source and this is advantageous from an economical point of view.

In the chemical substance detection method according to the present invention, the energy applied to an impurity having a larger mass number is higher than the energy applied to an impurity having a smaller mass number. Further, the chemical substance detection method according to the present invention is such that, when the frequency spectrum of a SWIFT waveform in which the voltage amplitude is increased as the frequency is smaller is converted so that the mass number is taken as an abscissa, the voltage amplitude per mass number is a substantially fixed value. Therefore, satisfactory energy is applied to an impurity having a larger mass number to remove it and energy in a required and satisfactory range can be applied to ions having small mass numbers, and thus the use efficiency of the energy can be improved, so that an excessively high power source apparatus is not required and hence the cost for the apparatus can be suppressed.

In the chemical substance detection apparatus according to the present invention, an impurity is removed using a SWIFT waveform which gives no voltage amplitude in the frequency bands corresponding to a plurality of detection object chemical substances. In addition, the detection object chemical substances are detected simultaneously by the mass analyzer. Thus, a plurality of detection object chemical substances are detected simultaneously and therefore, a measurement with high accuracy can be achieved and the precision of the combustion control can be improved.

In the chemical substance detection method according to the present invention, a plurality of detection object chemical substances are successively subjected to fragmentation in the order of from a detection object chemical substance having a smaller mass number to those having larger one. Therefore, all the detection object chemical substances can be detected and hence the sensitivity of mass analysis is improved, enabling a measurement with higher accuracy.

In the chemical substance detection method according to the present invention, the chemical substance detection method applies a TICKLE waveform comprising frequencies corresponding to at least two isotopes of the detection object chemical substance to subject at least two isotopes of the detection object chemical substance to fragmentation, making mass analysis. Thus, a plurality of isotopes are used in the mass analysis and therefore, even when a dioxin or a precursor thereof is present in an extremely slight amount in the exhaust gas, the accuracy of detection can be improved.

In the chemical substance detection method according to the present invention, at least two isotopes of fragments formed from the detection object chemical substance are subjected to mass analysis. Thus, a plurality of isotopes of fragments are used in the mass analysis and therefore, even when a dioxin or a precursor thereof is present in an extremely slight amount in the exhaust gas, the accuracy of detection can be improved.

In the chemical substance detection method according to the present invention, before the ion trapping step in the chemical substance detection method, energy higher than an ionization potential of the detection object chemical substance and lower than a sum of the ionization potential and dissociation energy of ions of the detection object chemical substance is applied to the detection object chemical substance to ionize the detection object chemical substance. In the chemical substance detection method according to the present invention, in the ionization step, energy higher than the ionization potential and equal to or smaller than a value of a sum of the ionization potential and 4 electron volts is applied to the detection object chemical substance. Therefore, unnecessary fragments are not generated, and the detection object chemical substance to be left is allowed to remain unbroken, making it possible to improve the detection sensitivity of mass analysis. By virtue of this effect as well as the above-mentioned action and effect obtained by the chemical substance detection method, the detection sensitivity of the mass analyzer is further improved, enabling a measurement with high accuracy.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

INDUSTRIAL APPLICABILITY

As mentioned above, the chemical substance detection apparatus and the chemical substance detection method according to the present invention are useful for detecting, with high accuracy, a dioxin or a precursor thereof contained in a very slight amount in the exhaust gas from, e.g., a refuse incineration system, and suitable for improving the rate of detection of a chemical substance to be detected to such an extent that the combustion conditions of a combustion furnace, such as a heating furnace, can be controlled even during the operation of the furnace.

The invention claimed is:

1. A chemical substance detection apparatus, comprising:
an ion trapping unit that traps, using any one of an electric field and a magnetic field, an ion group comprising ions of a chemical substance formed by ionization;
an arbitrary waveform generation unit that generates a SWIFT waveform having a first voltage amplitude in a first frequency band corresponding to an orbital resonance frequency of a first impurity present in a concentration, a second voltage amplitude in a second frequency band corresponding to an orbital resonance frequency of a second impurity present in the concentration, and zero voltage amplitude in a third frequency band corresponding to an orbital resonance frequency of the chemical substance, wherein signal intensities corresponding to the first impurity and the second impurity are a predetermined signal intensity or larger, and wherein the first voltage amplitude is larger than the second voltage amplitude; and
a mass analyzer that applies the SWIFT waveform generated in the arbitrary waveform generation unit to the ion group trapped by the ion trapping unit to remove the impurities, and then measures a mass of the chemical substance or a fragment thereof.

2. The chemical substance detection apparatus according to claim 1, further comprising an ionization unit that applies to the chemical substance energy higher than an ionization potential of the chemical substance and lower than a sum of the ionization potential and dissociation energy of ions of the chemical substance to ionize the chemical substance.

3. The chemical substance detection apparatus according to claim 2, wherein the ionization unit applies to the chemical substance energy higher than the ionization potential and equal to or smaller than a value of a sum of the ionization potential and 4 electron volts.

4. A chemical substance detection apparatus, comprising:
an ion trapping unit that traps, using any one of an electric field and a magnetic field, an ion group comprising ions of a chemical substance formed by ionization;
an arbitrary waveform generation unit that generates a SWIFT waveform in which a voltage amplitude is reduced as a frequency is increased; and
a mass analyzer that applies the SWIFT waveform to the ion group trapped by the ion trapping unit to remove the impurity, and then measures a mass of the chemical substance or a fragment thereof.

5. The chemical substance detection apparatus according to claim 4, further comprising an ionization unit that applies to the chemical substance energy higher than an ionization potential of the chemical substance and lower than a sum of the ionization potential and dissociation energy of ions of the chemical substance to ionize the chemical substance.

6. The chemical substance detection apparatus according to claim 5, wherein the ionization unit applies to the chemical substance energy higher than the ionization potential and equal to or smaller than a value of a sum of the ionization potential and 4 electron volts.

7. A chemical substance detection method, comprising:
an ion trapping step of trapping, using any one of an electric field and a magnetic field, an ion group comprising ions of a chemical substance formed by ionization;
an arbitrary waveform generation step of generating a SWIFT waveform having a first voltage amplitude in a first frequency band corresponding to an orbital resonance frequency of a first impurity present in a concentration, a second voltage amplitude in a second frequency band corresponding to an orbital resonance frequency of a second impurity present in the concentration, and zero voltage amplitude in a third frequency band corresponding to an orbital resonance frequency of the chemical substance, wherein signal intensities corresponding to the first impurity and the second impurity are a predetermined signal intensity or larger, and wherein the first voltage amplitude is larger than the second voltage amplitude; and
a mass analyzing step of applying the SWIFT waveform generated in the arbitrary waveform generation step to the ion group trapped in the ion trapping step to remove the impurities, and then measuring a mass of the chemical substance or a fragment thereof.

8. The chemical substance detection method according to claim 7, wherein the mass analyzing step includes measuring at least two members among isotopes of fragments formed from the chemical substance.

9. The chemical substance detection method according to claim 7, further comprising an ionization step of applying, before executing the ionization trap step, to the chemical substance energy higher than an ionization potential of the chemical substance and lower than a sum of the ionization potential and dissociation energy of ions of the chemical substance to ionize the chemical substance.

10. The chemical substance detection method according to claim 9, wherein the ionization step includes applying to the chemical substance energy higher than the ionization potential and equal to or smaller than a value of a sum of the ionization potential and 4 electron volts.

11. A chemical substance detection method, comprising:
an ion trapping step of trapping, using any one of an electric field and a magnetic field, an ion group comprising ions of a chemical substance formed by ionization;
an impurity removing step of applying a SWIFT waveform in which a voltage amplitude is reduced as a frequency is increased to remove an impurity from the chemical substance; and
a mass analyzing step of measuring a mass of the chemical substance or a fragment thereof.

12. The chemical substance detection method according to claim 11, wherein the mass analyzing step includes measuring at least two members among isotopes of fragments formed from the chemical substance.

13. The chemical substance detection method according to claim 11, further comprising an ionization step of applying, before executing the ionization trap step, to the chemical substance energy higher than an ionization potential of the chemical substance and lower than a sum of the ionization potential and dissociation energy of ions of the chemical substance to ionize the chemical substance.

14. The chemical substance detection method according to claim 13, wherein the ionization step includes applying to the chemical substance energy higher than the ionization potential and equal to or smaller than a value of a sum of the ionization potential and 4 electron volts.

15. A chemical substance detection method, comprising:
an ion tapping step of trapping, using any one of an electric field and a magnetic field, an ion group comprising ions of a plurality of chemical substances having different masses formed by ionization;
a step of applying to the ion group a SWIFT waveform which gives no voltage amplitude in a plurality of frequency bands corresponding to mass numbers of a plurality of chemical substances to remove an impurity while leaving the chemical substances;

a fragmentation step of fragmenting the chemical substance in an order of from a chemical substance having a smaller mass number to a chemical substance having a larger mass number; and a mass analyzing step of measuring masses of the chemical substances or the fragments thereof.

16. The chemical substance detection method according to claim 15, wherein the mass analyzing step includes measuring at least two members among isotopes of fragments formed from the chemical substance.

17. The chemical substance detection method according to claim 15, further comprising an ionization step of applying, before executing the ionization trap step, to the chemical substance energy higher than an ionization potential of the chemical substance and lower than a sum of the ionization potential and dissociation energy of ions of the chemical substance to ionize the chemical substance.

18. The chemical substance detection method according to claim 17, wherein the ionization step includes applying to the chemical substance energy higher than the ionization potential and equal to or smaller than a value of a sum of the ionization potential and 4 electron volts.

19. A chemical substance detection method, comprising:

an ion trapping step of trapping, using any one of an electric field and a magnetic field, an ion group comprising ions of a plurality of chemical substances having different masses formed by ionization;

a step of applying to the ion group a SWIFT waveform which gives no voltage amplitude in a plurality of frequency bands corresponding to mass numbers of a plurality of chemical substances to remove an impurity while leaving the chemical substances; and a fragmentation step of applying energy to at least two isotopes of the chemical substances by means of a TICKLE waveform comprising frequency components corresponding to the two isotopes to fragmentate the two isotopes; and a mass analyzing step of measuring masses of the chemical substances or the fragments thereof.

20. The chemical substance detection method according to claim 19, wherein the mass analyzing step includes measuring at least two members among isotopes of fragments formed from the chemical substance.

21. The chemical substance detection method according to claim 19, further comprising an ionization step of applying, before executing the ionization trap step, to the chemical substance energy higher than an ionization potential of the chemical substance and lower than a sum of the ionization potential and dissociation energy of ions of the chemical substance to ionize the chemical substance.

22. The chemical substance detection method according to claim 21, wherein the ionization step includes applying to the chemical substance energy higher than the ionization potential and equal to or smaller than a value of a sum of the ionization potential and 4 electron volts.

* * * * *